US009486535B2

(12) United States Patent
Wagner et al.

(10) Patent No.: US 9,486,535 B2
(45) Date of Patent: Nov. 8, 2016

(54) METHODS OF MAKING AND USING NANOSTRUCTURES

(71) Applicant: REGENTS OF THE UNIVERSITY OF MINNESOTA, St. Paul, MN (US)

(72) Inventors: Carston R. Wagner, St. Paul, MN (US); Jae Chul Lee, Dublin, OH (US); Sidath C. Kumarapperuma, Roseville, MN (US)

(73) Assignee: TYCHON BIOSCIENCE, LLC, Minneapolis, MN (US)

( * ) Notice: Subject to any disclaimer, the term of this patent is extended or adjusted under 35 U.S.C. 154(b) by 0 days.

(21) Appl. No.: 14/373,209

(22) PCT Filed: Jan. 18, 2013

(86) PCT No.: PCT/US2013/022218
§ 371 (c)(1),
(2) Date: Jul. 18, 2014

(87) PCT Pub. No.: WO2013/109939
PCT Pub. Date: Jul. 25, 2013

(65) Prior Publication Data
US 2015/0017189 A1 Jan. 15, 2015

Related U.S. Application Data

(60) Provisional application No. 61/588,621, filed on Jan. 19, 2012, provisional application No. 61/595,531, filed on Feb. 6, 2012, provisional application No. 61/695,775, filed on Aug. 31, 2012.

(51) Int. Cl.
| | | |
|---|---|---|
| A61K 47/48 | (2006.01) | |
| A61K 33/24 | (2006.01) | |
| A61K 31/7088 | (2006.01) | |
| C07D 475/08 | (2006.01) | |
| B82Y 5/00 | (2011.01) | |

(52) U.S. Cl.
CPC ..... *A61K 47/48561* (2013.01); *A61K 31/7088* (2013.01); *A61K 33/24* (2013.01); *A61K 47/481* (2013.01); *A61K 47/48061* (2013.01); *A61K 47/48092* (2013.01); *A61K 47/48746* (2013.01); *B82Y 5/00* (2013.01); *C07D 475/08* (2013.01); *Y10T 428/2982* (2015.01)

(58) Field of Classification Search
CPC ............... A61K 47/48561; A61K 47/48061; A61K 33/24; A61K 31/7088
See application file for complete search history.

(56) References Cited

U.S. PATENT DOCUMENTS

| | | | |
|---|---|---|---|
| 8,236,925 B1 * | 8/2012 | Wagner | 530/323 |
| 8,580,921 B2 * | 11/2013 | Wagner | 530/323 |
| 2003/0225007 A1 | 12/2003 | Tam et al. | |

FOREIGN PATENT DOCUMENTS

WO  WO 2011/059586 A2  5/2011

OTHER PUBLICATIONS

Baker, "Dendrimer-based nanoparticles for cancer therapy", *American Society of Hematology*, 708-719 (2009).
Carlson et al., "Chemically Controlled Self-Assembly of Protein Nanorings", *J. Am. Chem. Soc.* 128, 7630-7638 (2006).
Fegan et al., "Chemically Self-Assembled Antibody Nanostructures as Potential Drug Carriers", *Molecular Pharmaceutics*, 9(11), 3218-3227 (2012).
Gangar et al., "Programmable Self-Assembly of Antibody-Oligonucleotide Conjugates as Small Molecule and Protein Carriers", *Journal of the American Chemical Society*, vol. 134 (6), 2895-2897 (2012).
Kumarapperuma et al., "Biofunctionalization of dendrimer nanoparticles with DHFR-scFv's for targeted delivery, imaging and therapy in cancer", Abstract No. 133, Keystone Symposia on Molecular and Cellular Biology, Antibodies as Drugs, Keystone, CO, 2 pages, Feb. 6, 2011.
Kumarapperuma et al., "Biofunctionalization of dendrimer nanoparticles with DHFR-scFv's for targeted delivery, imaging and therapy in cancer", Poster, 1 page, Feb. 6, 2011.
Li et al., "Chemically Self-Assembled Antibody Nanorings (CSANs): Design and Characterization of an Anti-CD3 IgM Biomimetic", *Journal of the American Chemical Society*, vol. 132 (48), 17247-17257 (2010).
Li et al., "Self-assembly of antibodies by chemical induction", *Angew. Chem. Int. Ed.* 47, 10179-10182 (2008).
Muzykantov et al., "Streptavidin facilitates internalization and pulmonary targeting of an anti-endothelial cell antibody (platelet-endothelial cell adhesion molecule 1): A strategy for vascular immunoltargeting of drugs", *Proc. Natl. Acad. Sci*, 96, 2379-2384 (1999).
Patent Cooperation Treaty, International Searching Authority, Search Report and Written Opinion for PCT/US2013/022218, 13 pages, Mar. 14, 2013.
Wiewrodt et al., "Size-dependent intracellular immunotargeting of therapeutic cargoes into endothelial cells", *Blood* 99, 912-922 (2002).
Zhang et al., "Synthesis and ?Biological Evaluation of Bivalent Ligands for the Cannabinoid 1 Receptor", *J. Med. Chem.* 53, 7048-7060 (2010).
Zong et al., "Bifunctional PAMAM Dendrimer Conjugates of Folic Acid and Methotrexate with Defined Ratio", *Biomacromolecules* 13, 982-991 (2012).

\* cited by examiner

*Primary Examiner* — Yong Chu
(74) *Attorney, Agent, or Firm* — Viksnins Harris & Padys PLLP

(57) ABSTRACT

The invention provides methods for attaching drugs, dyes or radiolabels to bis-MTX. This method can be used to prepare bis-MTX analogs that can be used to deliver agents, such as nanoparticles, drugs, dyes or radiolabels, to cells.

14 Claims, 4 Drawing Sheets

METHODS OF MAKING AND USING NANOSTRUCTURES

CROSS-REFERENCE TO RELATED APPLICATIONS

This patent application claims the benefit of priority of U.S. application Ser. No. 61/588,621, filed Jan. 19, 2012, of U.S. application Ser. No. 61/595,531, filed Feb. 6, 2012, and of U.S. application Ser. No. 61/695,775, filed Aug. 31, 2012, which applications are herein incorporated by reference.

STATEMENT OF GOVERNMENT SUPPORT

This invention was made with government support under Grant Numbers CA120116 and CA125360 awarded by the National Institutes of Health. The government has certain rights in the invention.

BACKGROUND

Antibody drug conjugates (ADCs) have received considerable attention due to promising clinical results, with a therapeutic recently receiving FDA approval. (Alley et al., *Curr. Opin. Chem. Bio.* 2010, 14, 529-37; Katz et al., *Clin. Cancer Res.* 2011, 17 6428-36) The specific cell targeting, as directed by the antibody, allows for the use of extremely toxic small molecules, with the targeting resulting in reduced off target side effects. These properties have led to the possibility of resurrecting small molecule therapeutics, which have been discarded from the development pipeline due to unfavorable toxicities or pharmacokinetics. To date the predominant method of attaching drugs to antibodies has been via a covalent linkage; some of which can be cleaved intracellularly through chemical or enzymatic reactions. (Alley et al., *Curr. Opin. Chem. Bio.* 2010, 14, 529-37) The specificity afforded by antibodies (and antibody fragments) have also resulted in their use for the targeted delivery of liposomes, dendrimers, metallic nanoparticles and nanoparticles of non-metallic composition. (Cheng et al., *Expert Opin. Drug Deliv.* 2010, 7, 461-78; New et al., *Mol. Pharm.* 2012, 9, 374-81; Chattopadhyay et al., *Mol. Pharm.* 2012, 9, 2168-79; Tivnan et al., *PLoS One* 2012, 7, e38129) These species have been exploited for the delivery of therapeutic and imaging agents either through non-covalent encapsulation (Lehtinen et al., *PLoS One* 2012, 7, e41410) or covalent attachment. (New et al., *Mol. Pharm.* 2012, 9, 374-81) In some cases, e.g., gold nanoparticles and quantum dots, the nanoparticle may also be the therapeutic or imaging agent. (Melancon et al., *Biomaterials* 2011, 32, 7600-8; Ruan et al., *Biomaterials* 2012, 33, 7093-102)

Chemically self-assembled antibody nanorings (CSANs) can be formed through the oligomerization of dimeric dihydrofolate reductase antiCD3 single chain variable fragment (scFv) fusion proteins (DHFR$^2$antiCD3) with a bis-methotrexate (bisMTX) ligand (FIG. 1). (Li et al., *Angew. Chem. Int. Ed.* 2008, 47, 10179-82; Li et al. *J. Am. Chem. Soc.* 2010, 132, 17247-57). AntiCD3 CSANs are endocytosed upon binding to CD3+ T cells via a clathrin dependent mechanism, in a manner similar to that of the parental antiCD3 monoclonal antibody (mAb), UCHT-1. (Li et al. *J. Am. Chem. Soc.* 2010, 132, 17247-57) It was hypothesized that antiCD3 CSANs could be used for the delivery of dyes and drugs to T-leukemia cells for imaging and therapeutic purposes (FIG. 2). Control over ring size, and hence the valency of the displayed scFv, is possible through modification of the length and composition of the amino acid linker between the DHFR proteins: a 13 amino acid linker (13DHFR$^2$antiCD3) results in a mixture of monomeric and dimeric species; a shorter single glycine linker (1DHFR$^2$antiCD3) leads to predominantly octameric rings. (Li et al., *Angew. Chem. Int. Ed.* 2008, 47, 10179-82; Li et al., *J. Am. Chem. Soc.* 2010, 132, 17247-57; Carlson et al., *J. Am. Chem. Soc.* 2006, 128, 7630-8). This offers the possibility of controlling the number of therapeutic molecules delivered by the CSANs, as well as tuning the affinity for the targeted cells. Further the modular nature of the CSAN construct allows changes in size, valency, and loading of cargo. As these properties can modulate cellular endocytosis. (Muzykantov et al., *Proc. Natl. Acad. Sci. U.S.A.* 1999, 96, 2379-84; Wiewrodt et al., *Blood* 2002, 99, 912-22) CSANs are a useful construct for which to study these effects.

Despite the ability of the antiCD3 CSANs to selectively bind and undergo endocytosis, little is known about the intracellular behavior of these unique nanoparticles, or their ability to carry cargoes into cells. In part to address this issue, a unique trivalent bisMTX ligand was designed and synthesized. Molecules, such as dyes, radiolabels or drugs, can be attached. The attachment of a fluorophore has allowed verification of the ability of CSANs to act as a carrier. Also because the fluorescence of the dyes is quenched upon release from the CSANs, the intracellular stability of the CSANs was monitored under a variety of conditions. Further, CSANs can be disassembled intracellularly by DHFR inhibitors. To probe the potential for endosomal escape, while bisMTX is non-toxic to HPB-MLT (a T leukemia cancer cell line) antiCD3 CSAN mediated delivery resulted in an increase in cytotoxicity of at least 13-fold. Taken together, these results demonstrate that T-leukemia cells endocytose intact antiCD3 CSANs, which have a significant life-time in the cell, and that upon disassembly bisMTX is released into the cytoplasm.

SUMMARY OF CERTAIN EMBODIMENTS OF THE INVENTION

Certain embodiments of the present invention provide a compound of formula I:

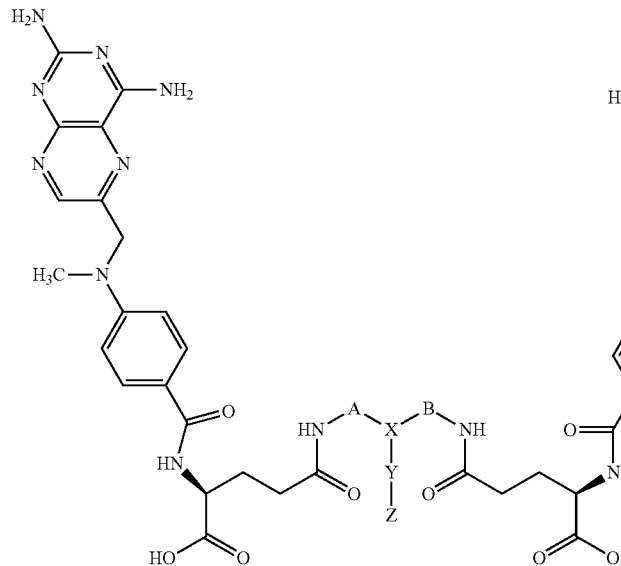

wherein:

A is a divalent, branched or unbranched, saturated or unsaturated, hydrocarbon chain, having from 2 to 25 carbon atoms (e.g., 3-10 carbon atoms in length, e.g., 5-10 carbon atoms in length), wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy;

B is a divalent, branched or unbranched, saturated or unsaturated, hydrocarbon chain, having from 2 to 25 carbon atoms (e.g., 3-10 carbon atoms in length, e.g., 5-10 carbon atoms in length), wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy;

X is N or

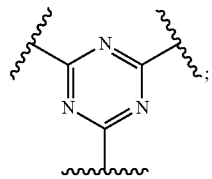 [SMILES: *c1nc(*)nc(*)n1];

Y is a suitable linking group, e.g., 8-25 atoms in length; and

Z is a functional group that can be used to covalently link the compound of formula I to an agent, such as a therapeutic or imaging agent.

In certain embodiments, A, B, and/or Y may be PEGylated.

In certain embodiments, A is a branched or unbranched $(C_2-C_{10})$alkylene chain wherein one or more carbon atoms is optionally replaced with an oxygen (—O—) oxygen atom in the chain.

In certain embodiments, A is a branched or unbranched $(C_5-C_{10})$alkylene chain.

In certain embodiments, A is an unbranched $(C_5-C_{10})$ alkylene chain.

In certain embodiments, B is a branched or unbranched $(C_2-C_{10})$alkylene chain wherein one or more carbon atoms is optionally replaced with an oxygen (—O—) oxygen atom in the chain.

In certain embodiments, B is a branched or unbranched $(C_5-C_{10})$alkylene chain.

In certain embodiments, B is an unbranched $(C_5-C_{10})$ alkylene chain.

In certain embodiments, X is N.

In certain embodiments, X is

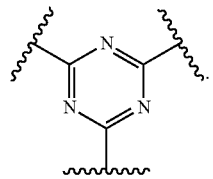 [SMILES: *c1nc(*)nc(*)n1].

It has been discovered that the structure of X is important for water solubilization and that N and

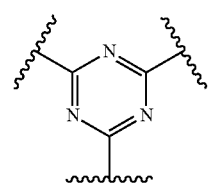 [SMILES: *c1nc(*)nc(*)n1]

can provide improved solubilization.

In certain embodiments, Y has a molecular weight of from about 20 daltons to about 20,000 daltons.

In certain embodiments, Y has a molecular weight of from about 20 daltons to about 5,000 daltons.

In certain embodiments, Y has a molecular weight of from about 20 daltons to about 1,000 daltons.

In certain embodiments, Y has a molecular weight of from about 20 daltons to about 200 daltons.

In certain embodiments, Y has a length of about 5 angstroms to about 60 angstroms.

In certain embodiments, Y separates Z from the remainder of the compound of formula I by about 5 angstroms to about 40 angstroms, inclusive, in length.

In certain embodiments, Y is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In certain embodiments, Y is a polyethyleneoxy chain comprising 2, 3, 4, 5, 6, 7, 8, 9, or 10 repeating ethyleneoxy units.

In certain embodiments, Y is a divalent radical formed from an amino acid or peptide.

In certain embodiments, the compound is a compound of the following formula

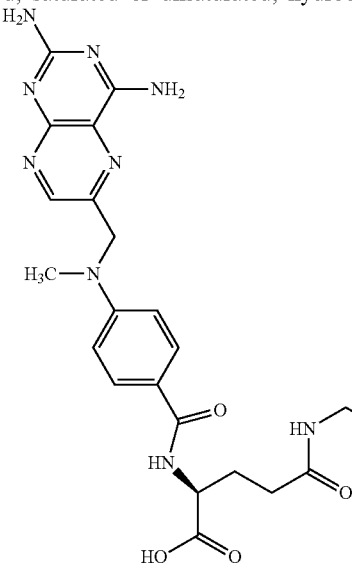
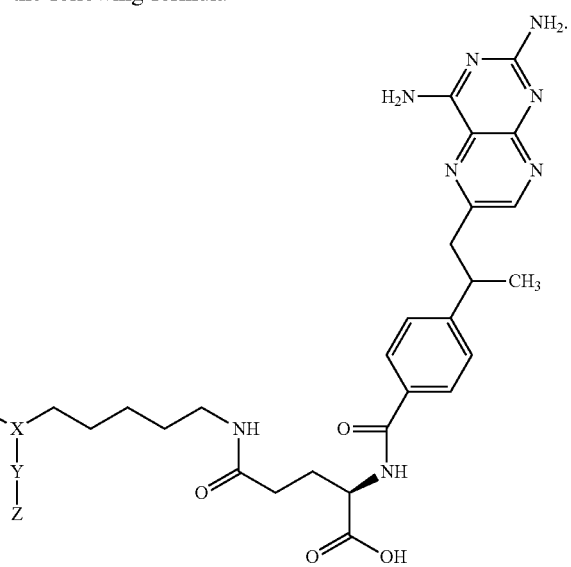

In certain embodiments, the compound is a compound of the following formula

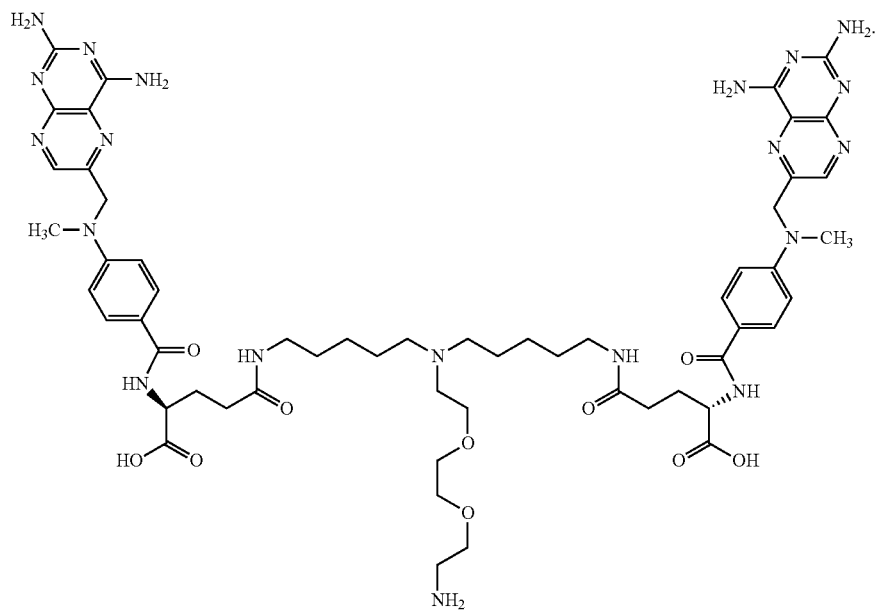

9, BisMTX-NH$_2$

In certain embodiments, Z is —OH, —SH, —NH$_2$, or —COOH.

Certain embodiments of the invention provide a conjugate comprising a compound of Formula I that is linked via Y to a therapeutic or imaging agent, wherein the conjugate further comprises a first dihydrofolate reductase (DHFR) molecule linked to second DHFR molecule via a linker. This conjugate may associate (e.g., self-assemble) with other similar conjugates to form a nanoring. (see, e.g., U.S. Pat. No. 8,236,925).

In certain embodiments, the conjugate further comprises a targeting molecule.

In certain embodiments, the targeting molecule selectively recognizes an antigen on a cancer cell.

In certain embodiments, the targeting molecule is a single-chain variable fragment (scFv).

In certain embodiments, the therapeutic or imaging agent is a first oligonucleotide.

In certain embodiments, the oligonucleotide is an antisense RNA molecule.

In certain embodiments, the conjugate further comprises a second oligonucleotide that is complementary to the first oligonucleotide, wherein the first and second oligonucleotide associate to form a duplex.

In certain embodiments, the duplex functions as an siRNA molecule.

In certain embodiments, the second oligonucleotide is linked directly or indirectly to a protein.

In certain embodiments, the second oligonucleotide is linked directly or indirectly to a small molecule.

In certain embodiments, the second oligonucleotide is linked indirectly to a protein via bis-methotrexate.

In certain embodiments, the second oligonucleotide is linked indirectly to a small molecule via bis-methotrexate.

In certain embodiments, the therapeutic or imaging is a nanoparticle.

In certain embodiments, the conjugate is linked to a nanoparticle.

In certain embodiments, the conjugate is in the form of a nanoring.

Certain embodiments of the invention provide a composition comprising a compound or conjugate as herein and a pharmaceutically acceptable carrier.

Certain embodiments of the invention provide a method for treating cancer in a patient in need of such treatment, comprising administering to the patient a therapeutically effective amount of a compound or conjugate as described herein.

Certain embodiments of the invention provide a compound or conjugate as described herein for use in medical treatment or diagnosis.

Certain embodiments of the invention provide the use of a compound or conjugate as described herein to prepare a medicament useful for treating cancer in an animal.

Certain embodiments of the invention provide a compound or conjugate as described herein for use in therapy.

Certain embodiments of the invention provide a compound or conjugate as described herein for use in treating cancer.

DETAILED DESCRIPTION

Figure 1:
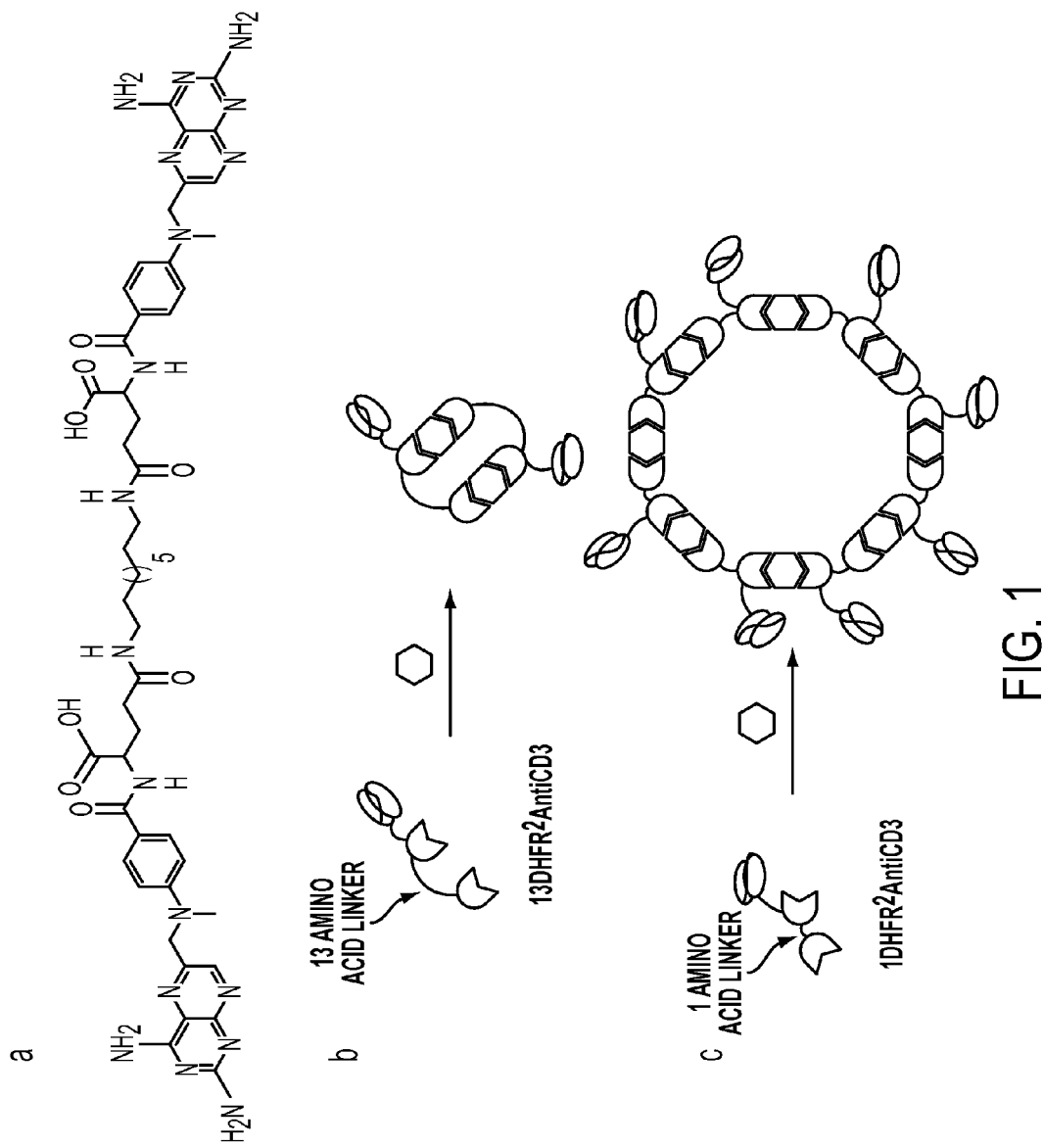
FIG. 1. a) Structure of bisMTX b) Formation of dimeric CSANs by incubation of 13DHFR$^2$antiCD3, with DHFR, antiCD3, and bisMTX c) Formation of octameric CSANs by incubation of 1DHFR$^2$antiCD3 with bisMTX.

Chemically self-assembled antibody nanorings (CSANs) displaying multiple copies of single chain variable fragments (scFv) can be prepared from dihydrofolate reductase (DHFR) fusion proteins and bis-methotrexate (BisMTX). A BisMTX chemical dimerizer (bisMTX-NH$_2$) has been designed and synthesized that contains a third linker arm that can be conjugated, e.g., to fluorophores, radiolabels and drugs. Mono-, divalent and higher order AntiCD3 CSANs were assembled with a FITC labeled bis-methotrexate ligand (bisMTX-FITC) and found to undergo rapid internalization and trafficking by the HPB-MLT, a CD3+ T-leukemia cell line, to the early and late endosome and lysosome. Since the fluorescence of bisMTX-FITC, when incorporated into CSANs, was found to be significantly greater than the free ligand, the stability of the endocytosed AntiCD3 CSANs could be monitored. The internalized CSANs were found to be stable for several hours, while treatment with the non-toxic DHFR inhibitor trimethoprim (TMP) resulted in a rapid loss (>80%) of cellular fluorescence within minutes, consistent with efficient intracellular disassembly of the nanorings. Over longer time periods (24 h) cellular fluorescence decreased by 75%-90%, whether or not cells had been treated with DMSO or trimethoprim. Although BisMTX is a potent inhibitor of DHFR, it was found to be non-toxic (IC$_{50}$>20 uM) to HPB-MLT cells. In contrast, AntiCD3 CSANs prepared with BisMTX were found to be at least 13-fold more cytotoxic (IC$_{50}$=1.0-1.5 uM) than BisMTX at 72 hours. Consistent with these findings from CSANs stability studies, no increase in cytotoxicity was observed upon treatment with trimethoprim. Taken together, the current results indicate that cell receptor targeting CSANs prepared with trifunctional BisMTX can be used as drug carriers, e.g., tissue selective drug carriers.

Described herein is the use of DHFR$^2$antiCD3 scFv fusion proteins for the targeted cellular delivery of single stranded oligonucleotides through attachment to bis-MTX, a ligand for DHFR$^2$ proteins. Oligonucleotide conjugated small molecules and proteins can be delivered to cells through formation of double stranded helices. The modular nature of this system will be useful for the delivery a variety of cargoes (e.g., nucleic acids, small molecules, proteins) to cells in which an internalizing scFv or peptide is known. Compared to other oligonucleotide conjugation approaches, the ease of the production of DHFR$^2$ fusion proteins, the robustness of the binding of DHFR$^2$ to bis-MTX and the control over binding stoichiometry are attractive features of this system. This system may also be useful for the delivery of functional nucleic acids, DNA nanostructures and proteins to cells and tissues.

As described herein, a method to self-assemble polyamidoamine dendrimer nanoparticles with dihydrofolate reductase linked single chain antibody fusion proteins (DHFR-scFv's) has been developed using a bis-methotrexate trilinker ligand. This assembly is reversible in vitro with FDA approved antibiotic trimethoprim. These nanoparticles have a diverse array of applications in diagnosis and therapy when DHFR-scFv's are self-assembled with functionalized dendrimers containing optical imaging agents, MRI contrast agents, genes and drugs. The specific delivery of self-assembled dendrimer-DHFR-anti-CD3 and dendrimer-DHFR-anti-CD22 scFv's to CD3+ T-leukemia (HPBMLT) and CD22+ B-lymphoma (Daudi) cells respectively was observed by confocal microscopy and MRI. Hence, this platform provides a multimodal nanocarrier drug delivery system for enhanced detection and treatment of human cancers.

Definitions

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, a-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine. The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

In certain embodiments of the invention Y is a linking group that joins the remainder of the compound of formula I to the group Z. The nature of the linking group Y is not critical provided the resulting compound retains the useful propertied described herein.

In one embodiment of the invention Y has a molecular weight of from about 20 daltons to about 20,000 daltons.

In one embodiment of the invention Y has a molecular weight of from about 20 daltons to about 5,000 daltons.

In one embodiment of the invention Y has a molecular weight of from about 20 daltons to about 1,000 daltons.

In one embodiment of the invention Y has a molecular weight of from about 20 daltons to about 200 daltons.

In another embodiment of the invention Y has a length of about 5 angstroms to about 60 angstroms.

In another embodiment of the invention Y separates the antigen from the remainder of the compound of formula I by about 5 angstroms to about 40 angstroms, inclusive, in length.

In another embodiment of the invention Y is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention Y comprises a polyethyleneoxy chain. In another embodiment of the invention the polyethyleneoxy chain comprises 2, 3, 4, 5, 6, 7, 8, 9, or 10 repeating ethyleneoxy units.

In another embodiment of the invention the Y is a divalent radical formed from a protein.

In another embodiment of the invention Y is a divalent radical formed from a peptide.

In another embodiment of the invention Y is a divalent radical formed from an amino acid.

Certain embodiments of the present invention provide a nanoparticle linked to a conjugate, wherein the conjugate comprises a first antifolate molecule linked to a second antifolate molecule via a first linker, wherein the first linker comprises a moiety that is conjugated to the nanoparticle. While the exemplary embodiments described herein describe the linkage of the conjugates to nanoparticles, the conjugates may also be linked to the surface of other suitable surfaces.

In certain embodiments, the first and second antifolate molecules are methotrexate molecules.

In certain embodiments, the conjugate further comprises a first dihydrofolate reductase (DHFR) molecule linked to second DHFR molecule via a second linker.

In certain embodiments, the compound or conjugate further comprises a targeting molecule.

In certain embodiments, the conjugate further comprises a targeting molecule.

In certain embodiments, the targeting molecule is a single-chain variable fragment (scFv).

In certain embodiments, the targeting molecule is a targeting peptide.

In certain embodiments, the targeting molecule selectively recognizes an antigen on a cancer cell.

Certain general categories and examples of antigens can be found at www.ncbi.nlm.nih.gov/books/NBK12961/ and in the Table below.

General Categories and Examples of Tumor Antigens

| Category | Example Antigen | Cancer Histology |
|---|---|---|
| Oncofetal | CEA | Colorectal carcinoma |
| | Immature laminin receptor | RCC |
| | TAG-72 | Prostate carcinoma |
| Oncoviral | HPV E6, E7 | Cervical carcinoma |
| Overexpressed/ accumulated | BING-4 | Melanoma |
| | Calcium-activated chloride channel 2 | Lung carcinoma |
| | Cyclin-$B_1$ | Multi |
| | 9D7 | RCC |
| | Ep-CAM | Breast carcinoma |
| | EphA3 | Multi |
| | Her2/neu | Multi |
| | Telomerase | Multi |
| | Mesothelin | Ductal pancreatic carcinoma |
| | SAP-1 | Colorectal carcinoma |
| | Survivin | Multi |
| Cancer-Testis | BAGE family | Multi |
| | CAGE family | Multi |
| | GAGE family | Multi |
| | MAGE family | Multi |
| | SAGE family | Multi |
| | XAGE family | Multi |
| CT9, CT10 | | Multi |
| | NY-ESO-1/LAGE-1 | Multi |
| | PRAME | Multi |
| | SSX-2 | Melanoma, Multi |
| Lineage Restricted | Melan-A/MART-1 | Melanoma |
| | Gp100/pmel17 | Melanoma |
| | Tyrosinase | Melanoma |
| | TRP-1/-2 | Melanoma |
| | P.polypeptide | Melanoma |
| | MC1R | Melanoma |
| | Prostate-pecific antigen | Prostate |
| Mutated | β-catenin | Melanoma, Prostate, HCC |
| | BRCA1/2 | Breast, ovarian carcinoma |
| | CDK4 | Multi |
| | CML66 | CML |
| | Fibronectin | Multi |
| | MART-2 | Melanoma |
| | p53 | Multi |
| | Ras | Multi |
| | TGF-βRII | Colorectal carcinoma |
| Posttranslationally altered | MUC1 | Ductal carcinoma, RCC |
| Idiotypic | Ig, TCR | B, T leukemia, lymphoma, myeloma |

BRCA = breast cancer antigen;
CDK4 = cyclin-dependent kinase-4;
CEA = carcino-embryonic antigen;
CML66 = chronic myelogenous leukemia (antigen) 66;
CT = cancer testis;
HPV = human papilloma virus;
Ep-CAM = epithelial cell adhesion molecule;
Ig = immunoglobulin;
MART-1/-2 = melanoma antigen recognized by T cells-1/-2;
MC1R = melanocortin-1-receptor;
SAP-1 = stomach cancer-associated protein tyrosine phosphatase-1;
TAG-72 = tumor antigen-72;
TCR = T cell receptor;
TGF-βRII = transforming growth factor-β receptor II;
TRP = tyrosinase-related protein.

From: Categories of Tumor Antigens, Holland-Frei Cancer Medicine. 6th edition, Kufe D W, Pollock R E, Weichselbaum R R, et al., editors. Hamilton (ON): BC Decker; 2003. Copyright© 2003, BC Decker Inc.

In certain embodiments, the targeting molecule is a single-chain variable fragment (scFv).

In certain embodiments, the conjugate further comprises a therapeutic agent.

In certain embodiments, the nanoparticle is a gold nanoparticle.

Certain embodiments of the present invention provide a composition comprising a nanoparticle as described herein and a pharmaceutically acceptable carrier.

Certain embodiments of the present invention provide a method for treating cancer in a patient in need of such treatment, comprising administering to the patient a therapeutically effective amount of a nanoparticle or composition as described herein.

Certain embodiments of the present invention provide a nanoparticle as described herein for use in medical treatment or diagnosis.

Certain embodiments of the present invention provide the use of a nanoparticle as described herein to prepare a medicament useful for treating cancer in an animal.

Certain embodiments of the present invention provide a nanoparticle as described herein for use in therapy.

Certain embodiments of the present invention provide a nanoparticle as described herein for use in treating cancer.

Certain embodiments of the invention are directed to the intermediates and derivatives described herein.

Certain embodiments of the invention are directed to the methods of making the nanoparticles, intermediates and derivatives described herein.

Certain embodiments of the invention provide a conjugate comprising a first antifolate molecule linked to a second antifolate molecule via a first linker, wherein the first linker further comprises at least a first oligonucleotide.

In certain embodiments, the first and second antifolate molecules are methotrexate molecules.

In certain embodiments, the conjugate further comprises a first dihydrofolate reductase (DHFR) molecule linked to second DHFR molecule via a second linker.

In certain embodiments, the conjugate further comprises a targeting molecule.

In certain embodiments, the targeting molecule selectively recognizes an antigen on a cancer cell.

In certain embodiments, the targeting molecule is a single-chain variable fragment (scFv).

In certain embodiments, the first oligonucleotide is a therapeutic agent.

In certain embodiments, the first oligonucleotide is an antisense RNA molecule.

In certain embodiments, the conjugate further comprises a second oligonucleotide that is complementary to the first oligonucleotide, wherein the first and second oligonucleotide associate to form a duplex.

In certain embodiments, the duplex functions as an siRNA molecule.

In certain embodiments, the second oligonucleotide is linked directly or indirectly to a protein.

In certain embodiments, the second oligonucleotide is linked directly or indirectly to a small molecule.

In certain embodiments, the second oligonucleotide is linked indirectly to a protein via a bis-antifolate molecule (e.g., bis-methotrexate).

In certain embodiments, the second oligonucleotide is linked indirectly to a small molecule via a bis-antifolate molecule (e.g., bis-methotrexate).

Certain embodiments of the invention provide a composition (e.g., a pharmaceutical composition) comprising a conjugate as described herein and a pharmaceutically acceptable carrier.

Certain embodiments of the invention provide a method for treating cancer in a patient in need of such treatment, comprising administering to the patient a therapeutically effective amount of a conjugate as described herein.

Certain embodiments of the invention provide a conjugate as described by herein for use in medical treatment or diagnosis.

Certain embodiments of the invention provide a use of a conjugate as described herein to prepare a medicament useful for treating cancer in an animal.

Certain embodiments of the invention provide a conjugate as described herein for use in therapy.

Certain embodiments of the invention provide a conjugate as described herein for use in treating cancer.

Certain embodiments of the invention provide the methods described herein for preparing the compounds and conjugates.

Certain embodiments of the invention will now be illustrated by the following non-limiting Examples.

Example 1

A branched bisMTX ligand with the third arm containing a primary amine 9, for the attachment of dyes (Scheme 1) was designed and synthesized. The synthesis of the bisMTX amine trilinker was achieved within seven convenient steps (Scheme 1). Initially the compound 2,2-(ethylenedioxy)bis(ethylamine) (1) was mono amine protected with di-tert-butyl dicarbonate (0.34 eq) and triethyl amine (1.7 eq) in dichloromethane. The resulting product (2) was refluxed with 5-bromovaleronitrile (2 eq) in the presence of potassium iodide (0.35 eq) and sodium carbonate (3 eq) in n-butanol to yield the tri-linker core assembly (3). Reductive hydrogenation of compound 3 with Raney-Ni did not go to completion despite several attempts with increasing amounts of the catalyst. However, the combination of Raney Ni and 10% Pd on C with 2 N NaOH in ethanol:tetrahydrofuran (4:1) completely reduced the nitrile to afford the diamine (4). The coupling of the diamine with N-carbobenzyloxy-L-glutamic acid 1-methyl ester (3 eq) in the presence of 1-ethyl-3-(3-dimethylaminopropyl)carbodiimide (EDC, 3.5 eq), 1-hydroxybenzotriazole (HOBt, 3.5 eq) and triethyl amine (10 eq) in dichloromethane provided the compound 5. Carboxybenzyl amine protections were then removed by Pd catalyzed hydrogenation to yield the compound 6. Subsequent EDC mediated coupling of compound 6 with pteroic acid derivative (Carlson et al., *I Am. Chem. Soc.* 2003, 125, 1501-7) (7) provided the fully protected trilinker (8). Deprotection of the tert-butyl carbonate groups with 5% trifluoroacetic acid in dichloromethane followed by the removal of methyl ester protections with 1M NaOH in methanol afforded the fully deprotected trilinker (9) in a total yield of 17%. The terminal primary amino acid in 9 can be used for attachment of a variety of moieties, via a stable amide bond. Initially, 9 was derivatized with fluorescein, through reaction with FITC to yield 10 (bisMTX-FITC).

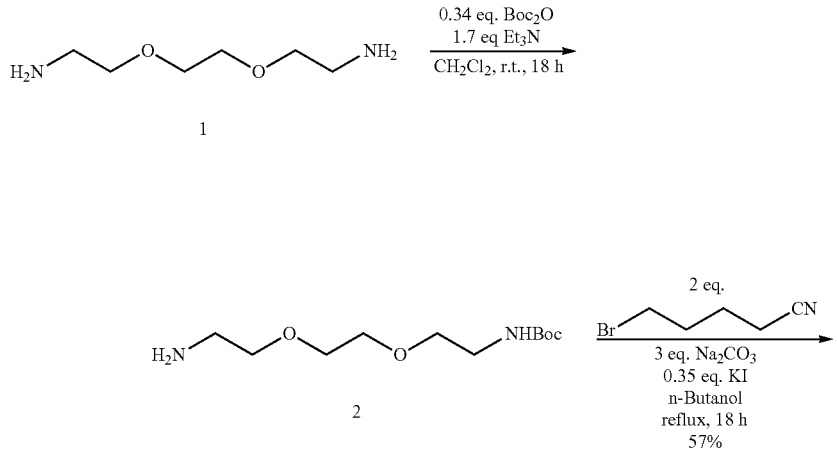

-continued
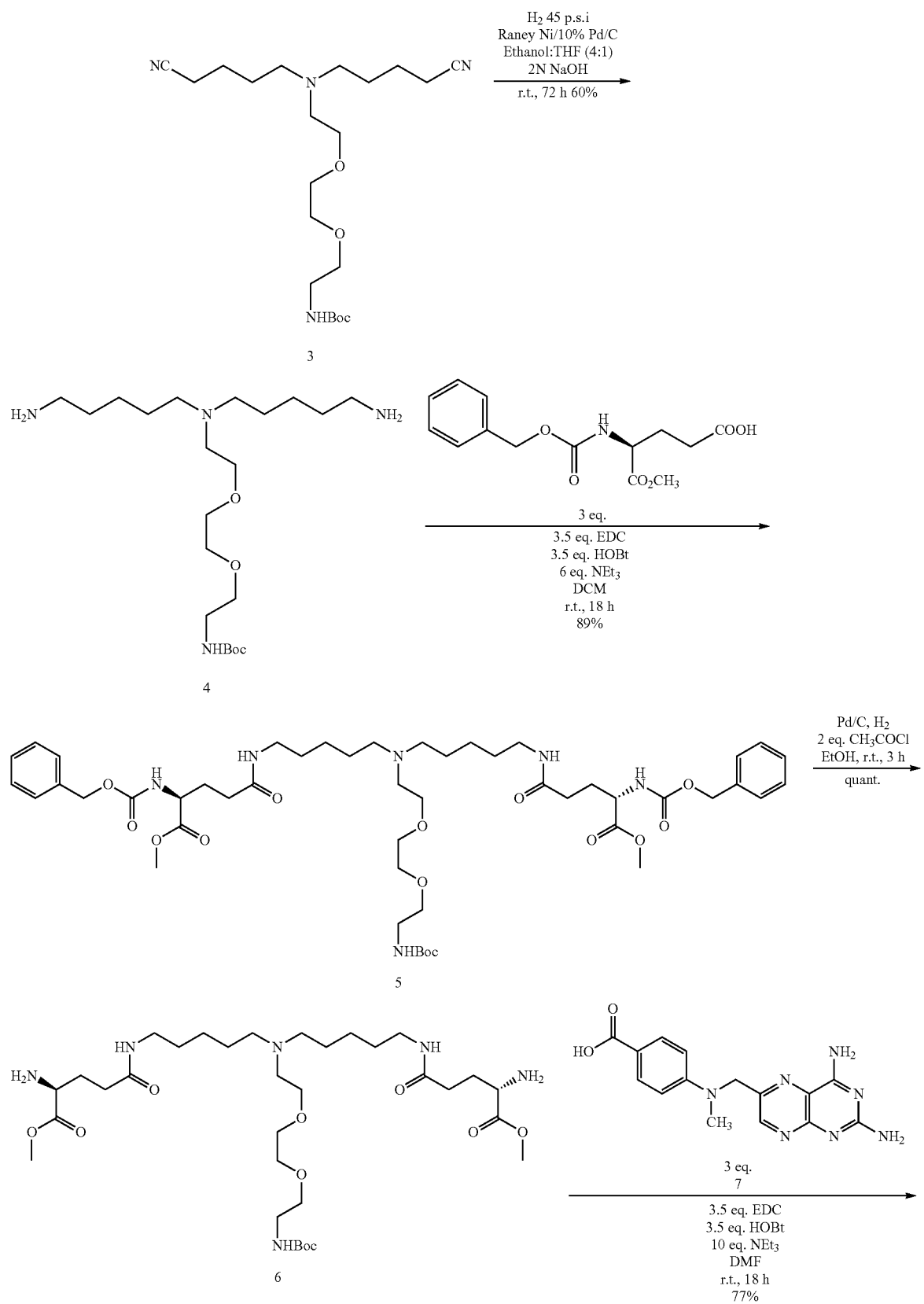

-continued
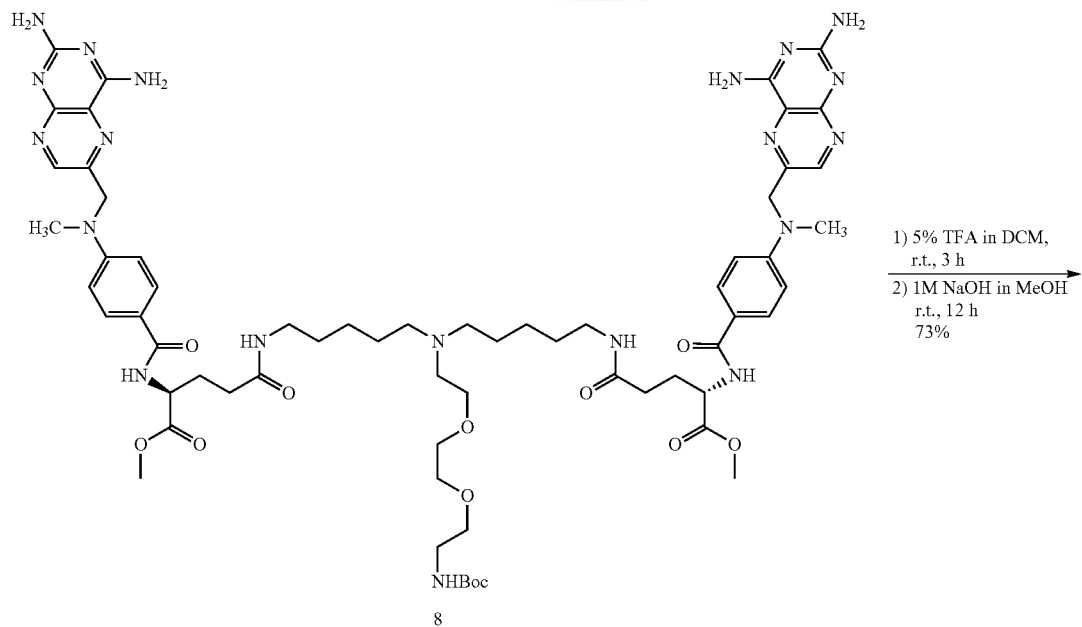
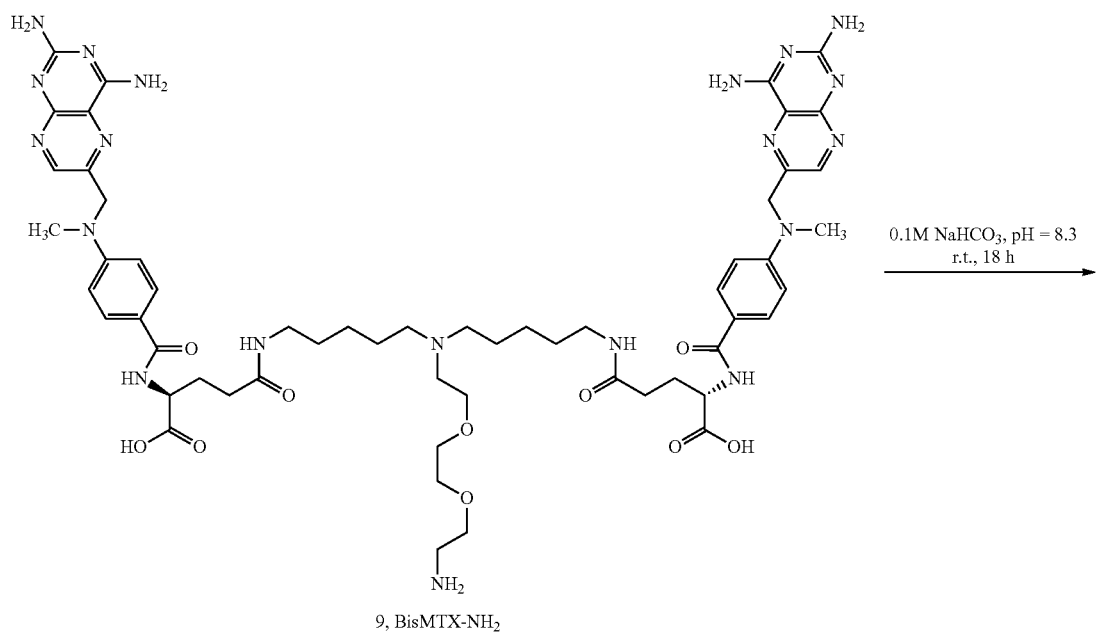

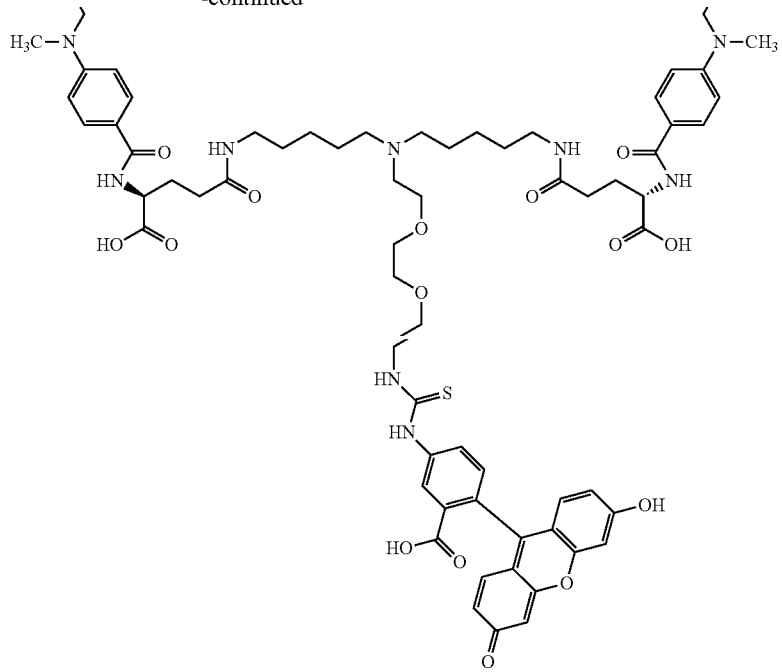

10, BisMTX-FITC

After incubation of 13DHFR²antiCD3 (the protein with the 13 amino acid linker between the DHFR proteins) with bisMTX-FITC size exclusion chromatography (SEC) analysis shows a mixture of dimeric and monomeric species similar to that observed upon incubation of the same protein with bisMTX (Li et al., *J. Am. Chem. Soc.* 2010, 132, 17247-57). Analysis of the SEC trace at 494 nm, the absorbance maximum for bisMTX-FITC, revealed that the monomer peak contained this absorbance, suggesting formation of an intramolecular macrocycle, comprising one 13DHFR²antiCD3 protein and one bisMTX-FITC ligand. Predominantly octameric CSANs are formed when bisMTX is mixed with 1DHFR²antiCD3 however, when bisMTX-FITC is used as the assembly agent, a distribution of smaller rings, ranging in size from dimer to hexamers were observable. A rationale for the change in the size preference for rings formed from 1DHFR²antiCD3 and 10 is not immediately evident.

In order to evaluate the interactions of bisMTX-FITC containing antiCD3 CSANs with CD3 positive cells, mixtures of bisMTX-FITC with either 13DHFR²antiCD3 or 1DHFR²antiCD3 were incubated with HPB-MLT cells. After washing, the cells were analyzed by flow cytometry. Increased fluorescence was observed for HPB-MLT cells that had been incubated with CSANs composed of bisMTX-FITC with either 13DHFR²antiCD3 or 1DHFR²antiCD3, relative to unstained HPB-MLT cells. The change in fluorescence was shown to be dependent on the concentration of the bisMTX-FITC containing CSANs, which were incubated with the HPB-MLT cells. Incubation of CSANs lacking antiCD3 scFvs (i.e. 13DHFR²) with HPB-MLT cells does not result in increased fluorescence, showing the necessity, as previously demonstrated, of antiCD3 scFvs for binding to the CD3+ cells. (Li et al., *Angew. Chem. Int. Ed.* 2008, 47, 10179-82; Li et al., *J. Am. Chem. Soc.* 2010, 132, 17247-57) When antiCD3 CSANs were incubated with CD3 negative Raji (B) cells no increased fluorescence was observed. Further evidence of the specific nature of the antiCD3 CSANs interactions with cell surface CD3 receptor was confirmed by the greatly reduced fluorescence observed when HPB-MLT cells were incubated with unlabeled monoclonal antiCD3, prior to addition of bisMTX-FITC containing CSANs. Together these experiments demonstrate that antiCD3 CSANs formed with bisMTX-FITC specifically bind to HPB-MLT cells via scFv targeted interactions with cell surface CD3.

To explore whether CSANs could deliver bisMTX-FITC intracellularly, HPB-MLT cells were incubated with a mixture of 13DHFR²antiCD3 and bisMTX-FITC at 37 or 4° C. and then visualized by fluorescence confocal microscopy. Cells incubated with the CSANs at 37° C. show internalized green punctates due to bisMTX-FITC fluorescence. The presence of intracellular green punctates is consistent with antiCD3 mediated endocytosis of the FITC containing CSANs. This is similar to what is observed when FITC labeled UCHT-1 mAb is incubated with HPB-MLT cells. (Li et al., *Angew. Chem. Int. Ed.* 2008, 47, 10179-82; Li et al., *J. Am. Chem. Soc.* 2010, 132, 17247-57) When CSANs are incubated with HPB-MLT cells at 4° C. the green fluorescence is observed on the cell membrane and no endocytosis is observed. This is consistent with an energy dependent endocytosis mechanism, which occurs upon scFv (or mAb) binding to CD3 cell surface receptors. (Li et al., *Angew. Chem. Int. Ed.* 2008, 47, 10179-82; Li et al., *J. Am. Chem. Soc.* 2010, 132, 17247-57) Monomeric and dimeric antiCD3 CSAN species as observed by SEC were purified and separately incubated with HPB-MLT cells. Similar patterns of internalization were observed for both monomeric and dimeric antiCD3 species. Incubation of bisMTX-FITC alone or CSANs formed by 13DHFR²antiCD22 (a B-cell specific scFv) and bisMTX-FITC with HPB-MLT cells resulted in no observable internalized fluorescence. CSANs formed by mixing 1DHFR²antiCD3 and bisMTX-FITC were also endocytosed by HPB-MLT cells, as visualized by the presence of internal green punctates. When bisMTX-FITC containing antiCD3 CSANs were incubated with HPB-MLT cells at 37° C. in the presence of Alexa Fluor 594 labeled transferrin (a marker of early endosomes( ) co-localization of red and green fluorescent punctuates was observed, indicating that antiCD3 CSANs carry the bisMTX-FITC into early endosomes (Dautry-Varsat et al., *Proc. Nat. Acad. Sci. USA* 1983 80, 2258-62). Further confocal experiments using a red dye to label lysosomes (LysoTracker red DND-99) revealed that the green punctates and lysosomes co-localize in a similar manner to FITC labeled UCHT-1 (Li et al., *J. Am. Chem. Soc.* 2010, 132, 17247-57). Thus, bisMTX-FITC was found to be internalized by the antiCD3 CSANs.

Dimeric antiCD3 CSANs prepared with bisMTX can undergo rapid disassembly in the presence of an excess of the DHFR inhibitor, trimethoprim (TMP) in PBS, pH 7.0. (Li et al., *J. Am. Chem. Soc.* 2010, 132, 17247-57) Similarly, treatment of CSANs prepared from bisMTX-FITC and 13DHFR$^2$antiCD3 with 2 mM trimethoprim resulted in conversion to the monomeric species as determined by SEC. During the course of investigations, it was discovered that that in solution the fluorescence of bisMTX-FITC relative to fluorescein was greatly quenched possibly due to hydrophobic stacking interactions between FITC and the two MTX moieties. (Carlson et al., *J. Am. Chem. Soc.* 2003, 125, 1501-7) However, after mixing 1DHFR$^2$antiCD3 with bisMTX-FITC, a 2-fold increase in FITC fluorescence was observed, which could be eliminated in a time dependent manner by the subsequent addition of excess trimethoprim. In the absence of trimethoprim, no decrease in fluorescence was observed over the same time period. Consequently, the assembly and disassembly of CSANs prepared from bisMTX-FITC can be monitored by observing the modulation of the incorporated fluorescein fluorescence.

Because trimethoprim is cell permeable, it was hypothesized that treatment of endocytosed CSANs prepared with bisMTX-FITC with trimethoprim would allow the observation their intracellular disassembly and release of bisMTX-FITC. After treating HPB-MLT cells with bisMTX-FITC containing CSANs, cells were washed and further incubated with non-toxic concentrations of trimethoprim (2 mM) for 3 hours at 37° C., before being visualized by fluorescence confocal microscopy. Cells treated with trimethoprim showed loss of green punctates while intracellular green fluorescent punctates were still observable in untreated cells. A similar loss of green punctates was observed when cells were treated with 0.5 mM pyrimethamine, a potent non-toxic inhibitor of bacterial and parasitic DHFR.

Due to the pH dependent nature of FITC fluorescence, it is possible that acidification of the endosomes during the incubation results in the decreased fluorescence. Extracellular experiments have shown that the fluorescence of bisMTX-FITC containing CSANs is reduced at pH 5.5, as compared to pH 7.0. However, this is unlikely the major cause of the observed decrease fluorescence, as the green fluorescence of the punctates remained stable for control cells that were not treated with trimethoprim. To further probe the possibility of pH dependence on the internalized CSANs, 9 was labeled with Pennsylvania Green (bisMTX-PG), a fluorescein analogue with pH independent fluorescent properties. (Mottram et al., *Org. Lett.* 2006 8, 581-4) A similar loss of fluorescence was observed with CSANs carrying bisMTX-PG when treated with trimethoprim or pyrimethamine, compared to untreated control cells.

To further examine the disassembly kinetics of bisMTX-FITC containing CSANs, a flow cytometry experiment was performed analyzing the time dependent decrease in fluorescence in the presence and absence of trimethoprim. HPB-MLT cells were treated with 150 nM CSANs composed of either 1DHFR$^2$antiCD3 or 13DHFR$^2$antiCD3 and bisMTX-FITC for one hour before being washed and incubated with either 2 mM trimethoprim or an equivalent volume of DMSO (as a control) at 37° C. for various time periods after which they were washed and fixed. Cells that were not treated with trimethoprim or DMSO, but were fixed after washing, were taken as time 0 and assumed to have 100% fluorescence. A rapid loss of fluorescence was observed for cells treated with bisMTX-FITC containing CSANs followed by trimethoprim. Within 15 minutes, the fluorescence for cells treated with 13DHFR$^2$antiCD3 and bisMTX-FITC CSANs followed by trimethoprim was reduced by 85% while a 60% loss of fluorescence was observed for cells that had been treated with 1DHFR$^2$antiCD3 and bisMTX-FITC CSANs followed by trimethoprim. By comparison, cells that were treated with DMSO, instead of trimethoprim, showed a significantly slower rate of decrease in fluorescence, with a loss of fluorescence of only 45% after 4 hours, whether previously treated with 1DHFR$^2$antiCD3 or 13DHFR$^2$antiCD3 bisMTX-FITC CSANs. In comparison, only 12% of the cellular fluorescence was lost over the same time period for HPB-MLT cells treated with fluorescein labeled parental monoclonal antibody, UCHT-1 (as a separate control), whether they were treated with DMSO or trimethoprim. In contrast, when cells that had internalized 1DHFR$^2$antiCD3 or 13DHFR$^2$antiCD3 bisMTX-FITC CSANs were treated with DMSO or trimethoprim for 24 hr, a similar decrease in fluorescence of 75% to 90%, respectively, was observed. These results imply that over time, disassembly of the endocytosed CSANs and release of bisMTX-FITC can occur in the absence of trimethoprim. In contrast, only a 50% loss of fluorescence was observed for HPB-MLT cells treated with FITC labeled UCHT-1 for 24 hours.

Taken together these experiments provide evidence that antiCD3 CSANs containing bisMTX-FITC are endocytosed by HPB-MLT cells and are partially stable intracellularly over 3-4 hours. In addition, treatment with small molecule inhibitors of DHFR results in the rapid intracellular disassembly of CSANs, while significant intracellular trimethoprim independent disassembly and release of bisMTX-FITC is observed over 24 hours. Nevertheless, the fluorescence quenching observed for bisMTX-FITC upon CSANs disassembly prevents monitoring bisMTX-FITC endosomal escape.

bisMTX ($K_i$=48 pM) is nearly as potent an inhibitor of murine DHFR as MTX ($K_i$=33 pM). (Pineda et al., *J. Med. Chem.* 2003 46, 2816-8) Since murine DHFR is 95% sequence identical to human DHFR, in comparison to MTX, the cytotoxicity of both 13DHFR$^2$antiCD3 and 1DHFR$^2$antiCD3-bisMTX CSANs was evaluated to HPB-MLT cells as an indicator of bisMTX endosomal escape upon CSAN disassembly (FIG. 1A). Treatment of HPB-MLT with bisMTX alone resulted in no observed toxicity after 72 h (IC$_{50}$>20 uM), while MTX inhibited cellular proliferation with an IC$_{50}$=0.6 uM and IC$_{80}$>50 uM. The inability of bisMTX to undergo folate receptor mediated internalization is likely responsible for its lack of activity relative to MTX, which may result from the strong preference of bisMTX for a folded conformation in aqueous solution. By comparison treatment for 72 h with 13DHFR$^2$antiCD3 or 1DHFR$^2$antiCD3 CSANs inhibited cellular proliferation with an IC$_{50}$=1.0-1.5 uM and an IC$_{80}$~2.5 uM. Consistent with the flow cytometry experiment showing that after 24 h the disassembly of CSANs is not significantly different for cells incubated in the presence or absence of trimethoprim (vide supra), treatment of the cells with trimethoprim following incubation of the cells with the CSANs for one hour had no affect on the observed cytotoxicity. These results are consistent with the release of bisMTX from the endosomal compartment, upon CSANs disassembly, thus resulting in likely DHFR inhibition and the observed cytotoxicity. The similar $IC_{50}$ values determined for both the dimeric and octameric CSANs may be due to differences in the levels of internalization, which may be affected by the size of the constructs. (Wiewrodt et al., *Blood* 2002, 99, 912-22)

In summary, a new water soluble bisMTX dimerizer has been prepared, bis-MTX-$NH_2$ (9) and demonstrated that it can be FITC labeled yielding bisMTX-FITC. Similar to bisMTX, mono- di- and multivalent CSANs fused to an anti-CD3 scFv were prepared with bisMTX-FITC. Once internalized, the bisMTX-FITC CSANs were shown to traffic to the early and late endosome and lysosome. Because bisMTX-FITC has a much higher fluorescence when incorporated into CSANs, the intracellular life time of the nanorings could be monitored. Disassembly of the CSANs and release of bisMTX-FITC could be achieved in minutes when the cells were treated with the non-toxic DHFR inhibitors, trimethoprim or pyrimethamine. If not treated with a DHFR antagonist, the CSANs were shown to persist in the endosomal compartments for several hours. While bisMTX, a potent DHFR inhibitor, was found to be non-toxic to T-leukemia cells expressing CD3, when incorporated into a mono- di- and multivalent antiCD3 CSANs, potent cytotoxicity was observable and thus consistent with endosomal release of bisMTX. Given the lack of bisMTX toxicity, bisMTX may have a decreased ability to cause MTX associated toxicities if inadvertently released from the CSANs during systemic circulation. Ongoing in vivo studies will clarify the validity of this hypothesis. The in vivo stability of the CSANs will be studied, as well as their biodistribution. In addition, results from studies of the design of CSANs prepared from bisMTX-$NH_2$ conjugated to an additional and releasable drug are in progress and will be reported in due course.

EXPERIMENTAL SECTION

General Methods

13DHFR$^2$antiCD3 and 1DHFR$^2$antiCD3 were prepared as described previously. (Li et al., *Angew. Chem. Int. Ed.* 2008, 47, 10179-82; Li et al., *I. Am. Chem. Soc.* 2010, 132, 17247-57) 13DHFR$^2$antiCD22 was prepared in a similar manner BisMTX was synthesized as described previously. (Wiewrodt et al., *Blood* 2002, 99, 912-22) HPB-MLT (T leukemia) and Raji (B lymphoma) cells were cultured in RPMI-1640 media (Lonza) supplemented with 10% (v/v) fetal bovine serum, L-Glutamine (2 mM final concentration), penicillin (100 units/mL), and streptomycin (100 µg/mL) in a humidified incubator with 5% $CO_2$ at 37° C.

Size Exclusion Chromatography

BisMTX-FITC (3 eq) was mixed with either 13DHFR$^2$antiCD3 or 1DHFR$^2$antiCD3 in P500 buffer (0.5 M NaCl, 50 mM $KH_2PO_4$, 1 mM EDTA, pH 7) and incubated at room temperature for approximately 10 minutes. The CSAN solution was injected onto a Superdex G200 size exclusion column (Amersham Biosciences, USA) and eluted with P500 buffer at 0.5 mL/min.

Fluorescence Confocal Microscopy

BisMTX-FITC (or BisMTX-PG) and the appropriate DHFR fusion protein were mixed (250 nM) and added to $0.5 \times 10^6$ HPB-MLT cells at either 4 or 37° C. for 1 hr in RPMI media. Cells were then pelleted by centrifugation (400×g, 5 min). After being washed twice with PBS (phosphate buffered saline) cells were incubated on Poly-Prep slides coated with poly-L-Lysine (Sigma) at 4 or 37° C. for 30 mins. Cells were then fixed with 4% paraformaldehyde solution for 10 mins and washed thrice with PBS. Finally, cells were treated with ProLong Gold Antifade reagent with DAPI (Invitrogen), a cover slip was applied.

After overnight incubation, images were taken within inner sections of the cells by sequential scanning using a fluorescence confocal microscopy using an Olympus FluoView 1000 BX2 Upright Confocal microscope. Resulting images are the compression of 3-5 z-axis slices. For disassembly experiments after the initial one hour incubation cells were washed twice with PBS before being resuspended in media containing 2 mM trimethoprim, 0.5 mM pyrimethamine or DMSO for three hours at 37° C. after which time they were processed as above. Early endosome co-localization experiments were performed by incubating cells with antiCD3 CSANs or FITC labeled UCHT-1 with Alexa Fluor 594 labeled transferrin (Life Technologies) for 30 minutes at 37° C. before washing and continuing slide preparation as above. Lysosomes were labeled by incubating cells with media containing LysoTracker red DND-99 (Life Technologies) for 1 hour at 37° C., in the presence of CSANs or FITC labeled UCHT-1, before washing and slide preparation as above.

Flow Cytometry $1 \times 10^6$ HPB-MLT (or Raji) cells were treated with BisMTX-FITC containing CSAN constructs at the required concentrations at 4° C. for 1 hr in PBS buffer (containing 0.05% BSA and 0.1% sodium azide). Cells were centrifuged (400×g, 10 min), washed twice with PBS/BSA/sodium azide buffer before being resuspended in the same buffer. Their fluorescence was analyzed with a FACSCalibur flow cytometer (BD Biosciences). For competition experiments, HPB-MLT cells were incubated with 40 nM UCHT-1 on ice for 10 mins prior to addition BisMTX-FITC CSAN constructs anti-CD3 constructs (100 nM) followed by washing as above. For disassembly experiments HPB-MLT cells were treated with 150 nM CSANs or 3.95 nM UCHT-1 FITC for 1 hour at 37° C. before being washed twice with RPMI media and finally resuspended in media. The cells ($0.5 \times 10^6$) were aliquoted into 1 mL of media containing either 2 mM trimethoprim or DMSO and incubated at 37° C. for the required period of time. Cells were then pelleted, washed once with PBS buffer and fixed with 0.5% paraformaldehyde in PBS buffer. Samples were stored at 4° C. in the dark until analyzed.

Cytotoxicity Analysis $2.5 \times 10^4$ HPB-MLT cells were mixed with the appropriate concentration of antiCD3 CSANs in a total volume of 90 uL and incubated at 37° C. for one hour. Then 10 uL media containing trimethoprim (or an equivalent volume of DMSO) was added to give a final concentration of 250 µM before the cells were incubated at 37° C. for 72 hours. Control cells were incubated with either 250 µM trimethoprim or DMSO. Cell viability was determined using CellTiter 96 AQueous Non-Radioactive Cell Proliferation Assay (Promega).

Methods

All reagents and solvents were of highest quality available and were used directly unless otherwise described. Reactions were performed in an efficient fume hood equipped with continuous argon and vacuum lines. Reactions involving air sensitive material were carried out in an argon atmosphere. All NMR spectra were taken at default temperature (~20° C.). ¹H NMR spectra were recorded on a Varian 400 MHz NMR spectrometer. Chemical shifts are reported in ppm relative to the solvent signal. ESI-MS analyses were done on a Bruker BioTOF II mass spectrometer. Thin-layer chromatography (TLC) was performed on Analtech (Newark, Del.) general purpose silica gel on polyester plates with fluorescent indicator, and spots were visualized with UV light or, by staining with anisaldehyde or Ninhydrin. Flash column chromatography was performed using regular gravity columns or ISCO-Combiflash Companion with Isco Redisep normal phase or reverse phase C 18 columns. HPLC purifications were performed on a Beckman Coulter instrument (126 solvent module, 168 PDA detector) equipped with a Higgins Analytical —HAISIL C-8, 5 um Semiprep column (250×10 mm).

1) Synthesis of N—BOC-2,2'-(ethylenedioxy)bis(ethylamine) (2)

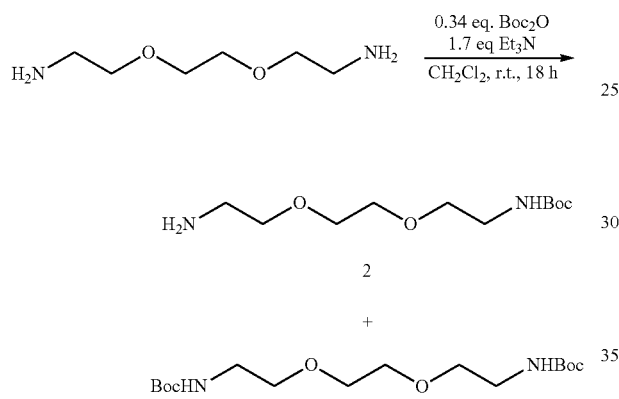

To a stirring solution of 2,2'-(Ethylenedioxy)bis(ethylamine) (7.26 mL, 50 mmol) and anhydrous triethylamine (11.8 mL, 85 mmol) in dry $CH_2Cl_2$ (100 mL) in an ice bath was added dropwise a solution of di-tert-butyl dicarbonate (3.71 g, 17 mmol) in dry $CH_2Cl_2$ (20 mL) over 15 minutes. Then the reaction mixture was allowed to reach the room temperature and continued stirring overnight. The resulting white suspension was washed with sat. $NaHCO_3$ (100 mL) and brine (100 mL). The organic layer was dried over anhydrous sodium sulfate, filtered, solvents evaporated and dried under a high vacuum to yield a mixture of mono (major product) and di-protected product (3.86 g). This material was used in the next reaction without further purification. ESI-MS calcd for mono $C_{11}H_{24}N_2O_4$ $[M+H]^+$ 249.1814, found 249.1896; calcd for di-protected $C_{16}H_{32}N_2O_6Na$ $[M+Na]^+$ 371.2158, found 371.2258.

2) Synthesis of Compound 3

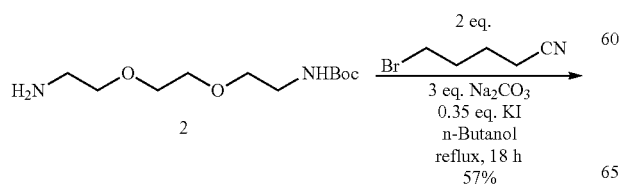

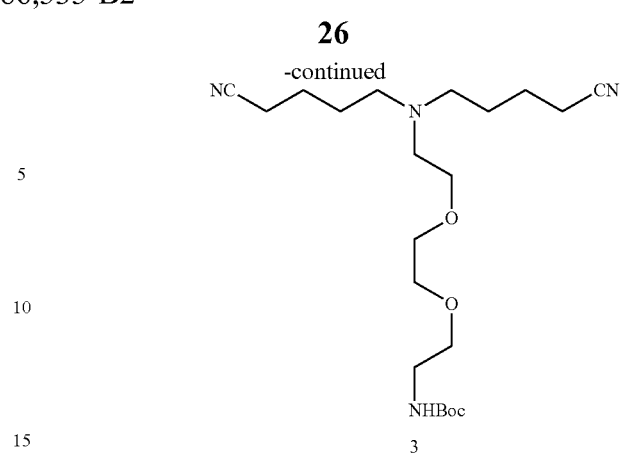

To a stirring suspension of 2 (2.98 g, 12.0 mmol) sodium carbonate (3.82 g, 36.0 mmol), and potassium iodide (0.70 g, 4.2 mmol) in n-butanol (100 mL) at 115° C. was added dropwise 5-bromovaleronitrile (2.80 mL, 24.0 mmol) in n-butanol (20 mL). The reaction was refluxed overnight (18 hrs). Then the reaction was filtered and the solid was washed with diethyl ether. The product was then extracted into 1 M HCl, which was then made basic with solid sodium carbonate and the product extracted back into diethyl ether. The organic layer was dried over anhydrous sodium sulfate, filtered and evaporated to yield the compound 3 as a colorless oil (2.80 g, 57%, over 2 steps). ¹H NMR (400 MHz, $CDCl_3$) δ 4.972 (br. s, 1H), 3.591 (s, 4H), 3.538 (m, 4H), 3.315 (d, 2H), 2.645 (t, 2H), 2.497 (t, 4H), 2.385 (t, 4H), 1.701 (m, 4H), 1.649 (m, 4H), 1.446 (s, 9H). ESI-MS calcd for $C_{21}H_{39}N_4O_4$ $[M+H]^+$411.2966, found 411.2979.

3) Synthesis of Compound 4

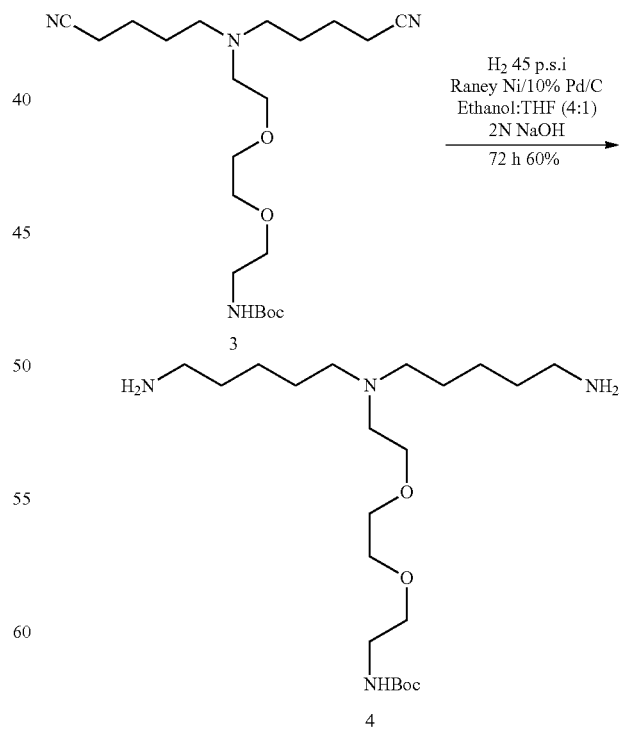

A solution of 3 (1.15 g, 2.80 mmol) in EtOH:THF (4:1, 100 mL) in a Parr flask was added Raney Ni (1.5 g, 50% suspension in water), 10% palladium on carbon (0.3 g) and 2 N NaOH (35 mL) and shaken under 45 psi hydrogen pressure for 72 hrs at room temp. The catalyst was filtered off on celite, solvents removed in vacuo and a mixture of water (100 mL) and methylene chloride (100 mL) was added. After phase separation aqueous phase was extracted with methylene chloride (3×50 mL) and combined organic phase was dried over anhydrous sodium sulfate, filtered and solvents were removed in vacuo to obtain 4 as a colorless oil (0.7 g, 60%). $^1$H NMR (400 MHz, CDCl$_3$) δ 8.161 (s, 1H), 5.531 (s, 2H), 5.132 (s, 2H), 3.595 (m, 4H), 3.537 (m, 4H), 3.318 (d, J=5.1 Hz, 2H), 2.75-2.57 (m, 6H), 2.50-2.38 (m, 4H), 1.66-1.39 (m, 17H), 1.35-1.15 (m, 4H). ESI-MS calcd for $C_{21}H_{46}N_4O_4Na$ [M+Na]$^+$ 441.3423, found 441.3411.

4) Synthesis of Compound 5 g, 10.5 mmol) in DCM was added N-Carbobenzyloxy-L-glutamic acid 1-methyl ester (2.65 g, 8.97 mmol) and anhydrous triethylamine (2.5 mL, 18 mmol) under Ar. The reaction mixture was stirred overnight, diluted with CH$_2$Cl$_2$ (40 mL), washed with Sat. NaHCO$_3$ (50 mL), 5% KH$_2$PO$_4$ (50 mL), water (50 mL) and brine (50 mL) The organic phase was dried over anhydrous Na$_2$SO$_4$, filtered and solvents were removed. The crude product was purified by flash chromatography (5-20% CH$_3$OH in CH$_2$Cl$_2$) to provide 5 as a white foam (2.6 g, 89%). $^1$H NMR (400 MHz, CDCl$_3$) δ 7.341 (m, 10H), 6.23 (br. s, 2H), 5.89 (br. s, 2H), 5.095 (s, 4H), 4.33 (m, 2H), 3.728 (s, 6H), 3.572 (m, 6H), 3.515 (t, J=5.1 Hz, 2H), 3.29 (d, J=4.8 Hz, 2H), 3.202 (dd, J=12.7, 6.5

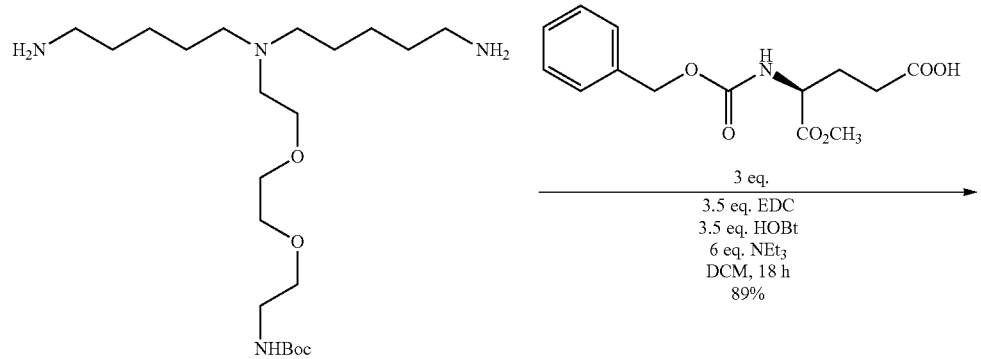

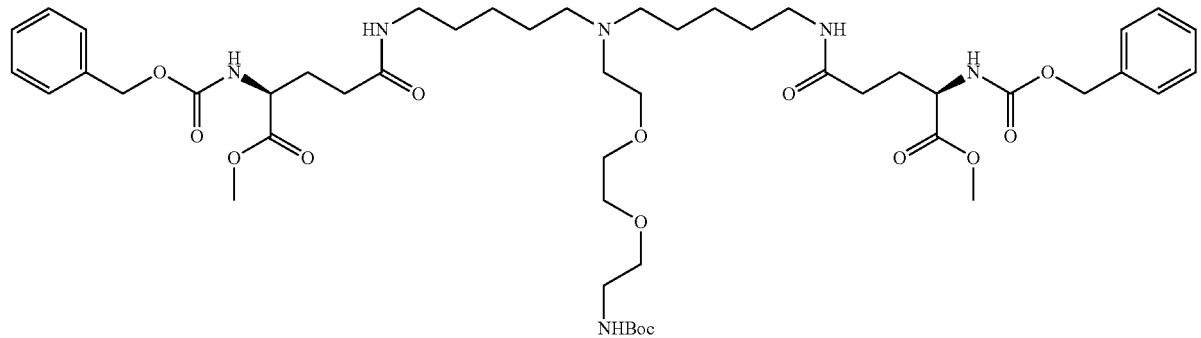

To a stirring solution of 4 (1.26 g, 3.01 mmol), N-(3-dimethylaminopropyl)-N'-ethylcarbodiimide hydrochloride (2.01 g, 10 mmol) and 1-hydroxybenzotriazole hydrate (1.61

Hz, 4H), 2.76 (br. s, 2H), 2.57 (br. s, 3H), 2.26 (m, 6H), 1.97 (m, 4H), 1.44 (m, 17H), 1.37-1.22 (m, 4H). ESI-MS calcd for $C_{49}H_{77}N_6O_{14}$ [M+H]$^+$ 973.5492, found 973.5509.

5) Synthesis of Compound 6

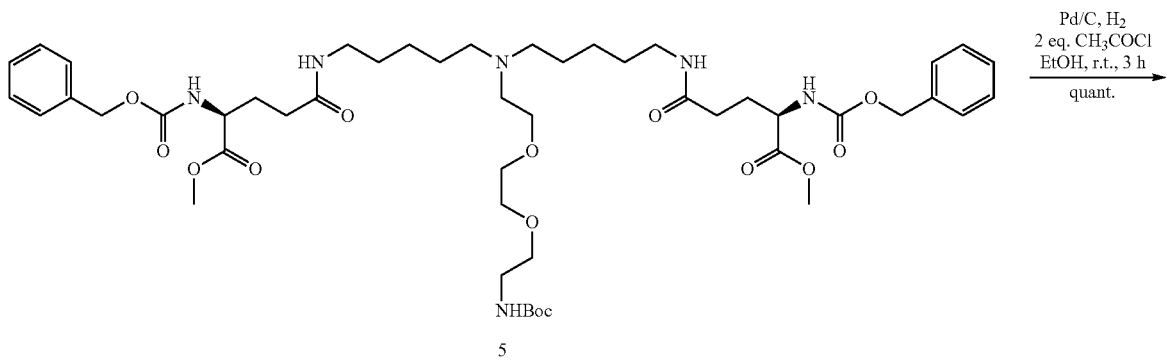

The compound 5 (2.43 g, 2.50 mmol) was dissolved in a solution of acetyl chloride (0.35 mL, 5.0 mmol) in methanol (30 mL) under Ar. Then 10% palladium on carbon was added and flushed with Ar. The mixture was flushed with hydrogen and a H$_2$ balloon was attached. The reaction mixture was stirred vigorously for 3 hrs (reaction was monitored by TLC). Then the reaction mixture was diluted with 4× methanol and filtered through celite. The filtrate was evaporated and dried under vacuum to yield the compound 6 as a white foam (1.8 g, quant.). %). $^1$H NMR (400 MHz, DMSO-d$_6$) δ 7.976 (br. t, 3H), 3.849 (t, 2H), 3.693 (s, 6H), 3.642 (m, 2H), 3.497 (m, 4H), 3.350 (m, 10H), 3.014 (m, 8H), 2.215 (m, 4H), 1.928 (m, 4H), 1.537 (m, 4H), 1.420-1.320 (overlapping s and m, 13H), 1.225 (m, 4H). ESI-MS calcd for C$_{33}$H$_{65}$N$_6$O$_{10}$ [M+H]$^+$705.4757, found 705.4771.

6) Synthesis of Compound 8

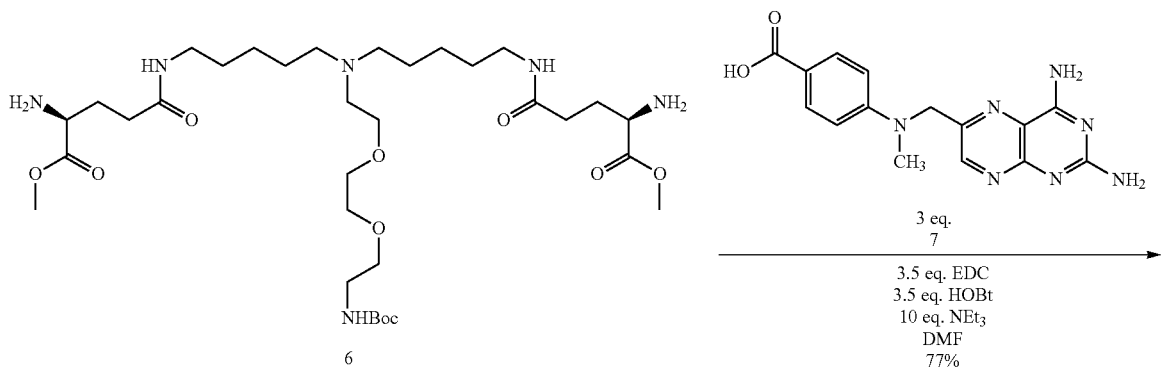

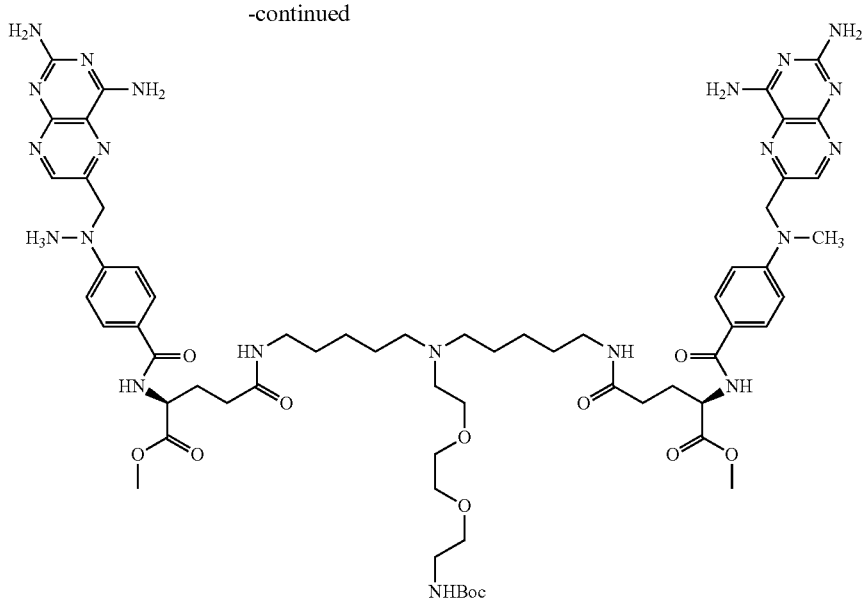

8

To a stirring solution of 6 (0.7 g, 1 mmol), N-(3-dimethylaminopropyl)-N'-ethylcarbodiimide hydrochloride (0.67 g, 3.5 mmol) and 1-hydroxybenzotriazole hydrate (0.54 g, 3.5 mmol) in anhydrous dimethyl formamide (20 mL) was added 7¹ (0.98 g, 3.0 mmol). Then anhydrous triethylamine (1.4 mL, 10 mmol) was added dropwise to the reaction mixture under Ar and continued stirring for 18 hrs. After evaporating the solvents the resulting slurry was loaded on to silica and purified by flash chromatography (0-20% $CH_3OH$/1% $Et_3N$ in $CH_2Cl_2$/1% $Et_3N$) to provide 8 as a yellow solid (1.0 g, 77%). Second flash chromatographic purification (0-20% $CH_3OH$/1% $Et_3N$ in $CH_2Cl_2$/1% $Et_3N$) was necessary to remove minor impurities (0.66 g, 45%). ESI-MS calcd for $C_{63}H_{92}N_{20}O_{12}$ $[M+2H]^{2+}$ 660.3602, found 660.3612.

7) Synthesis of bisMTX-$NH_2$ trilinker (9)

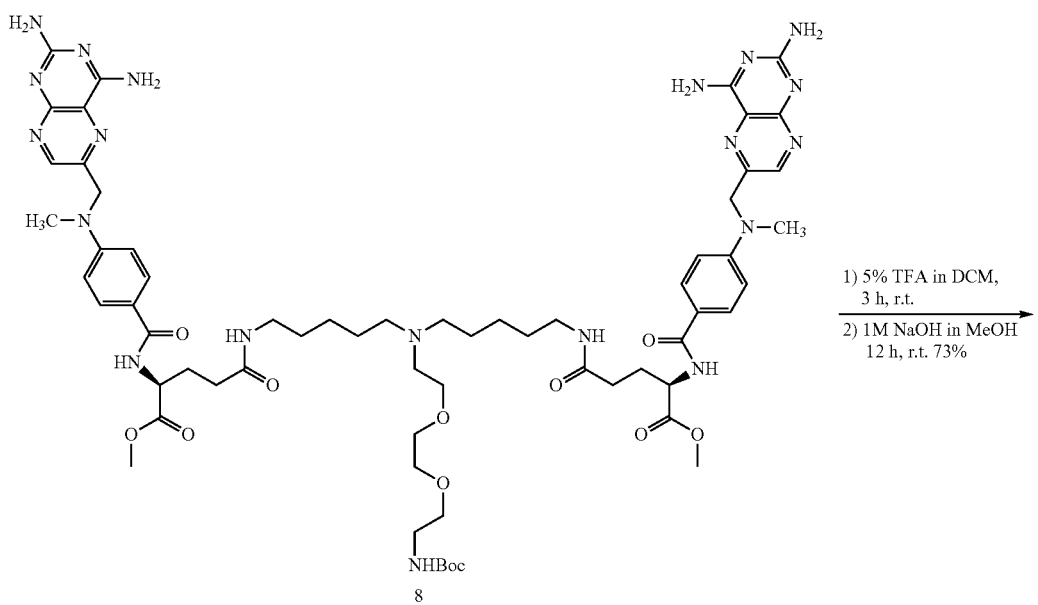

8

1) 5% TFA in DCM, 3 h, r.t.
2) 1M NaOH in MeOH 12 h, r.t. 73%

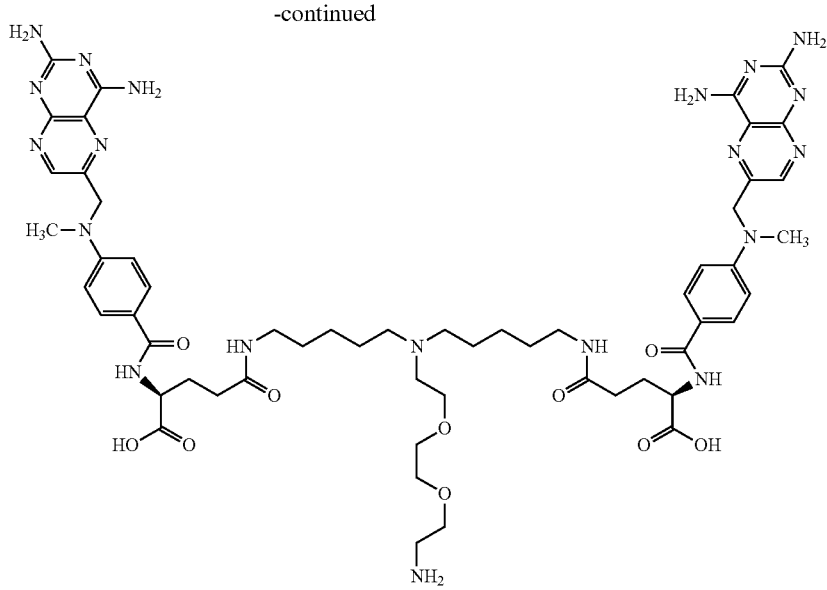

9, BisMTX—NH₂

A solution of compound 8 (0.30 g, 0.23 mmol) in 5% v/v trifluoroacetic acid/dichlormethane was stirred at room temperature for 3 hrs. After evaporating the solvents, crude product was re-dissolved in dicholoromethane and evaporated 3 times to remove any excess trifluoroacetic acid. Completion of the reaction was confirmed by ESI-MS (MS calcd for $C_{58}H_{83}N_{20}O_{10}$ $[M+2H]^{2+}$ 610.20, found 610.34). This crude product was then dissolved in 1M NaOH in methanol (10 mL) and stirred overnight at room temperature in the dark. Reaction mixture was neutralized with acetic acid and desalted by loading on to a C18-Sep-Pak reverse phase cartridge and eluting with 50% acetonitrile in water. The resulting solution was lyophilized and further purified by HPLC using a C-8 semi-prep reverse phase column (mobile phase gradient 2%-50% acetonitrile/0.1% trifluoroacetic acid in water/0.1% trifluoroacetic acid) to obtain the final product 9 (0.20 g, 73%). ¹H NMR (400 MHz, CD₃OD) δ 8.518 (s, 2H), 7.75 (d, J=8 Hz, 4H), 6.85 (d, J=8 Hz, 4H), 4.905 (s, 4H), 4.526 (m, 2H), 3.801 (m, 2H), 3.686, (m, 6H), 3.366 (m, 3H), 3.264-3.060 (overlapping s and m, 17H), 2.460-2.26 (overlapping m, 6H), 2.059 (m, 2H), 1.710 (m, 4H), 1.537 (m, 4H), 1.371 (m, 4H). ESI-MS calcd for $C_{56}H_{79}N_{20}O_{10}$ $[M+2H]^{2+}$ 596.3183, found 596.3238.

Synthesis of bisMTX-FITC trilinker (10)

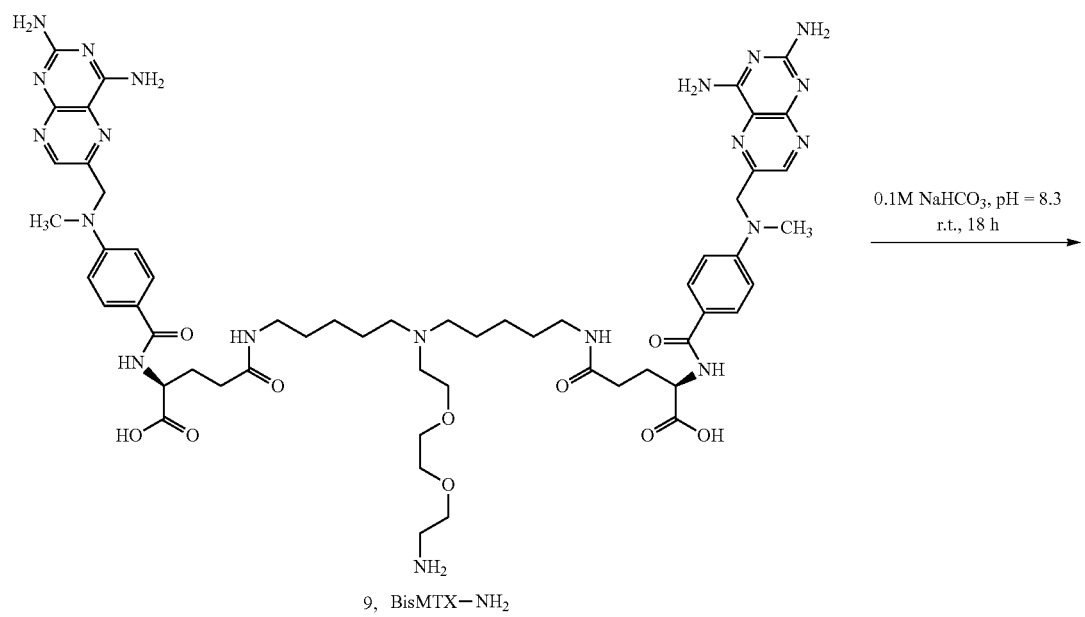

9, BisMTX—NH₂

-continued

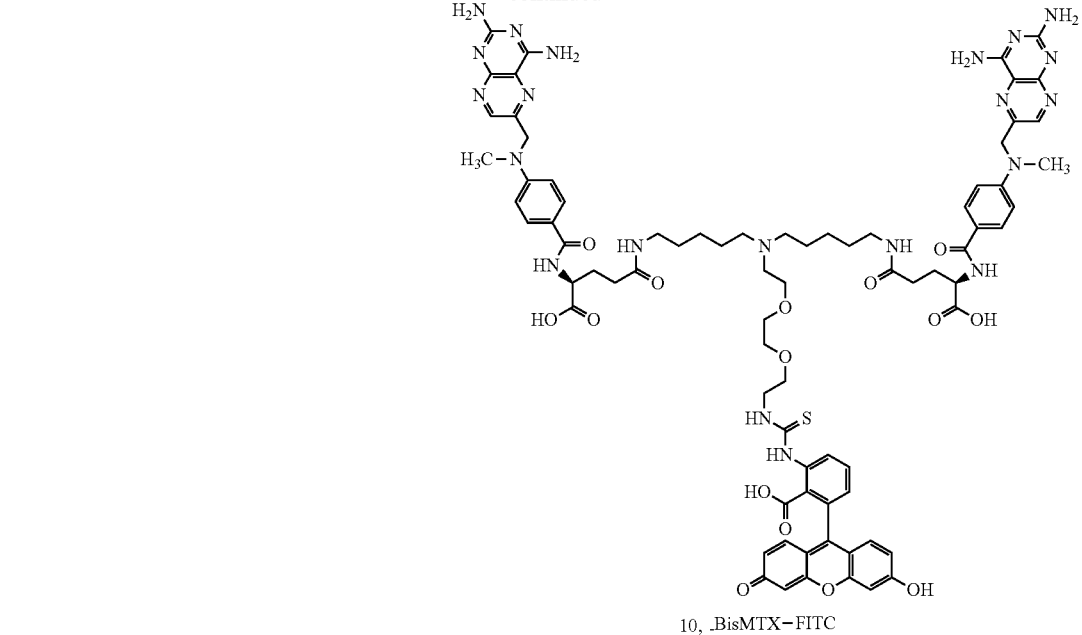

10, BisMTX-FITC

A solution of compound 9 (2.5 mg, 2.1 μmol) was dissolved in 2 mL 0.1 M sodium bicarbonate buffer (pH 8.5). Separately, FITC (1 mg, 2.5 μmol was dissolved in anhydrous DMF and added to the solution of 9. After stirring overnight the product was purified by HPLC using a C-8 semi-prep reverse phase column (mobile phase gradient 2%-50% acetonitrile/0.1% trifluoroacetic acid in water/0.1% trifluoroacetic acid) to obtain the final product 10 (2.1 mg, 63%).

ESI-MS calcd for $C_{77}H_{91}N_{21}O_{15}S_1$ [M+2H]$^{2+}$ 790.8357, found 790.8437.

Synthesis of bisMTX-PG trilinker (11)

9 (2 mg, 1.7 μmol) was dissolved in anhydrous DMF (1 mL) and triethylamine (1.4 uL, 10 μmol) was added followed by Pennsylvania Green N-hydroxysuccinimide ester[2] (0.96 mg, 2 mop. The solution was stirred overnight at room temperature and the product was purified by HPLC using a C-8 semi-prep reverse phase column (mobile phase gradient 2%-50% acetonitrile/0.1% trifluoroacetic acid in water/0.1% trifluoroacetic acid) to obtain the final product 11 (1.2 mg, 45%). ESI-MS calcd for $C_{77}H_{90}N_{20}O_{14}F_2$ [M+2H]$^{2+}$ 778.3451, found 778.3531.

Synthesis of Triazine Trivalent Dimerizers

Triazine trivalent dimerizers can be prepared with methods similar to those described hereinabove, e.g., as described in the following scheme.

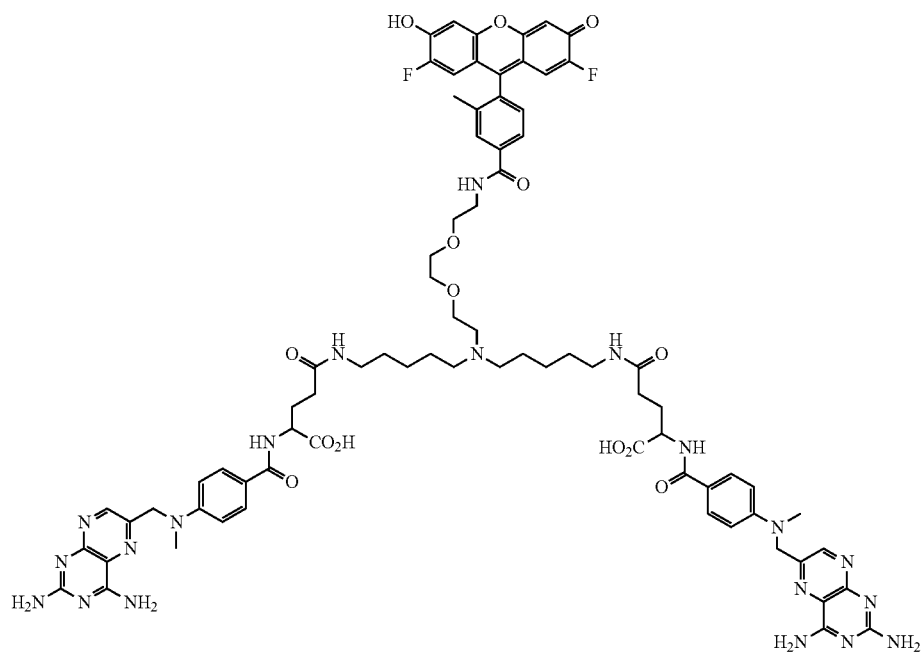

11

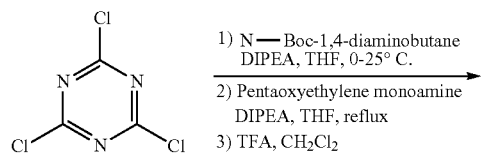
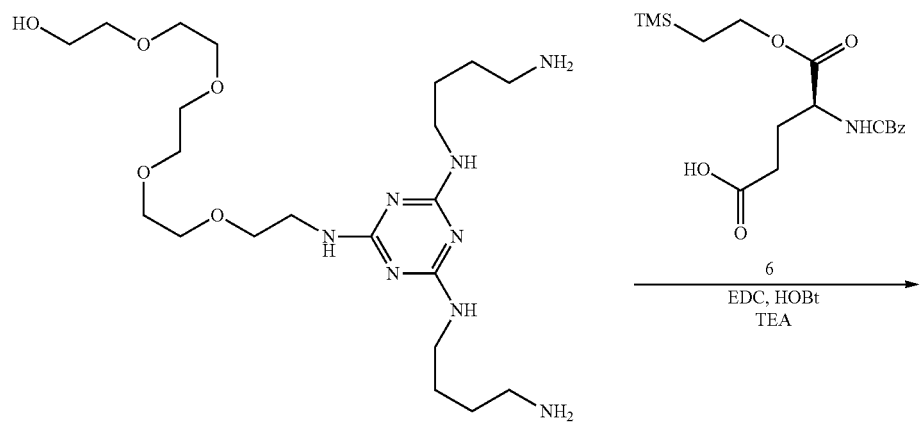
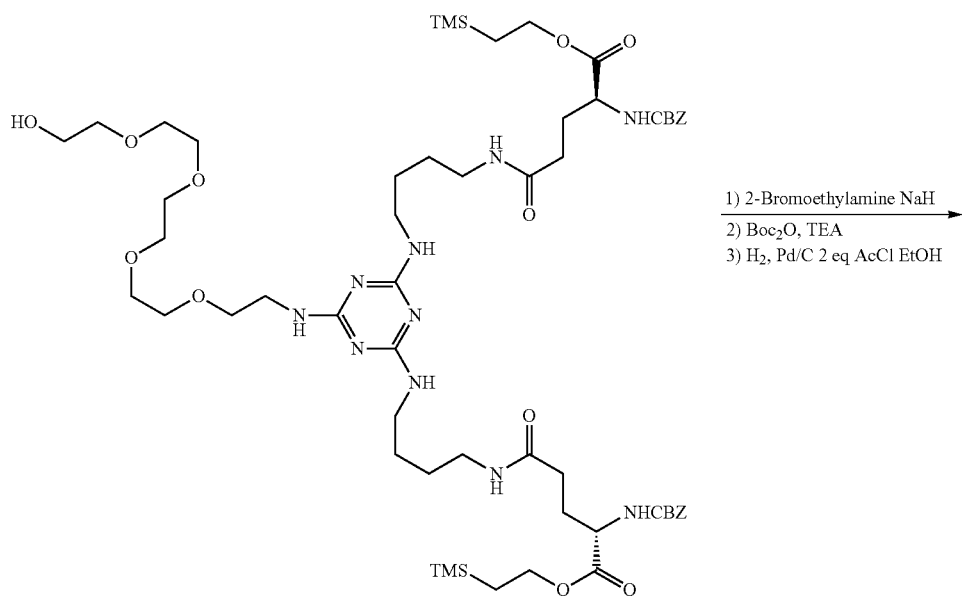

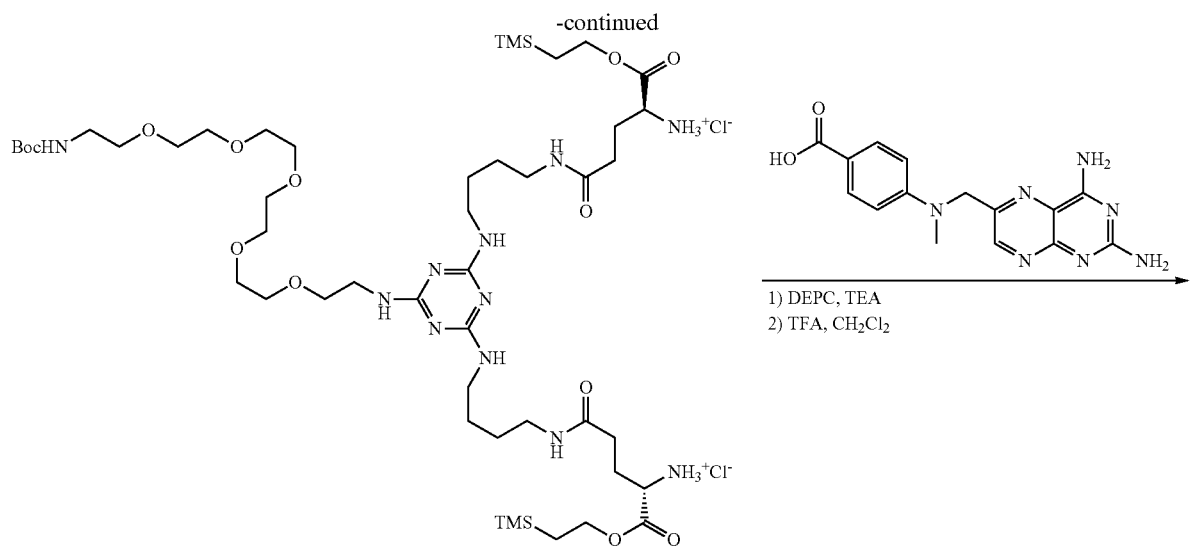

The triazine-based MTX dimer 14 will be prepared with the commercially available cyanuric chloride. Temperature-controlled, stepwise substitution of the triazine ring has been accomplished as described (Neerman et al., Mol. Pharmaceutics. 2004, 1, 390-393; Steffensen et al., Angew. Chem.-Inter. Ed. 2004, 43, 5178-5180) to yield the trialkylated triazine 11 in a yield of 70-75%, after deprotection with trifluoroacetic acid (TFA). (Carlson et al, J. Am. Chem. Soc. (2003), 125, 1501; Mottram et al, Org. Lett (2007), 9, 3741)

Abbreviations

CSAN, chemically self-assembled antibody nanorings; Cbz, carboxybenzyl; DMSO, dimethyl sulfoxide; FITC, fluorescein isothiocyanate; mAb, monoclonal antibody; MTX, methotrexate; Pyr, pyrimethamine; SEC, size exclusion chromatography; TMP, trimethoprim;

Example 2A Biofunctionalization of Nanoparticles for Targeted Delivery, Imaging and Therapy Multifunctional nanoparticles, e.g., single chain antibody (scFv) linked multifunctional nanoparticles, have an immense potential for cancer imaging and therapy as targeted delivery agents due to scFv's having high specificity, high affinity, lower immunogenicity and smaller size. However, currently-available technologies do not provide adequate multifunctional nanoparticles, e.g., because the nanoparticles do not exhibit the stability needed for biomedical use. As described herein, a method to self-assemble polyamidoamine dendrimer nanoparticles with dihydrofolate reductase linked single chain antibody fusion proteins (DHFR-scFv's) has been developed using a bis-methotrexate tri-linker ligand. This assembly is reversible in vitro with FDA approved antibiotic trimethoprim. These nanoparticles have a diverse array of applications in diagnosis and therapy when DHFR-scFv's are self-assembled with functionalized dendrimers containing optical imaging agents, MRI contrast agents, genes and drugs. The specific delivery of self-assembled dendrimer-DHFR-anti-CD3 and dendrimer-DHFR-anti-CD22 scFv's to CD3+ T-leukemia (HPBMLT)

and CD22+ B-lymphoma (Daudi) cells respectively was observed by confocal microscopy and MRI. Hence, this platform provides a multimodal nanocarrier drug delivery system for enhanced detection and treatment of human cancers.

The self-assembly of proteins by controlled dimerization of dihydrofolate reductase (DHFR) with bis-methotrexate (bis-MTX) ligands and disassembly with the FDA approved antibiotic trimethoprim has been investigated. (Carlson et al., *J. Am. Chem. Soc.* 2006, 128, 7630; and Li et al., *Angew. Chem. Int. Ed.* 2008, 47, 10179.) As described herein, the dimerizer has been modified with a third arm to incorporate a variety of functionalities including dyes, metal chelators and drugs. Accordingly, targeted delivery by effectively bio-functionalizing a dendrimer is described herein.

As described herein, a versatile DHFR dimerizer has been created that can be functionalized with variety of agents including dyes, chelators, therapeutic drugs and nanoparticles for imaging and therapy. Successful cell internalization of the multifunctional dendrimer-based nanoparticle has shown its potential to be used as a multi modality nanotherapeutic agent. This nanoparticle will be useful as a contrast agent for in vivo tumor imaging, e.g., Gd-MRI.

$DHFR_2$-antiCD22 fusion proteins delivering nanoparticles to Daudi cells (Human Burkitt's lymphoma cells) have been imaged. $DHFR_2$-antiCD3 fusion proteins delivering nanoparticles to HPB-MLT cells (T Leukemia cells) have been imaged.

Scheme A depicts the synthesis of a trilinker ligand and nanoparticle construction, and Table A depicts properties of the nanoparticles.

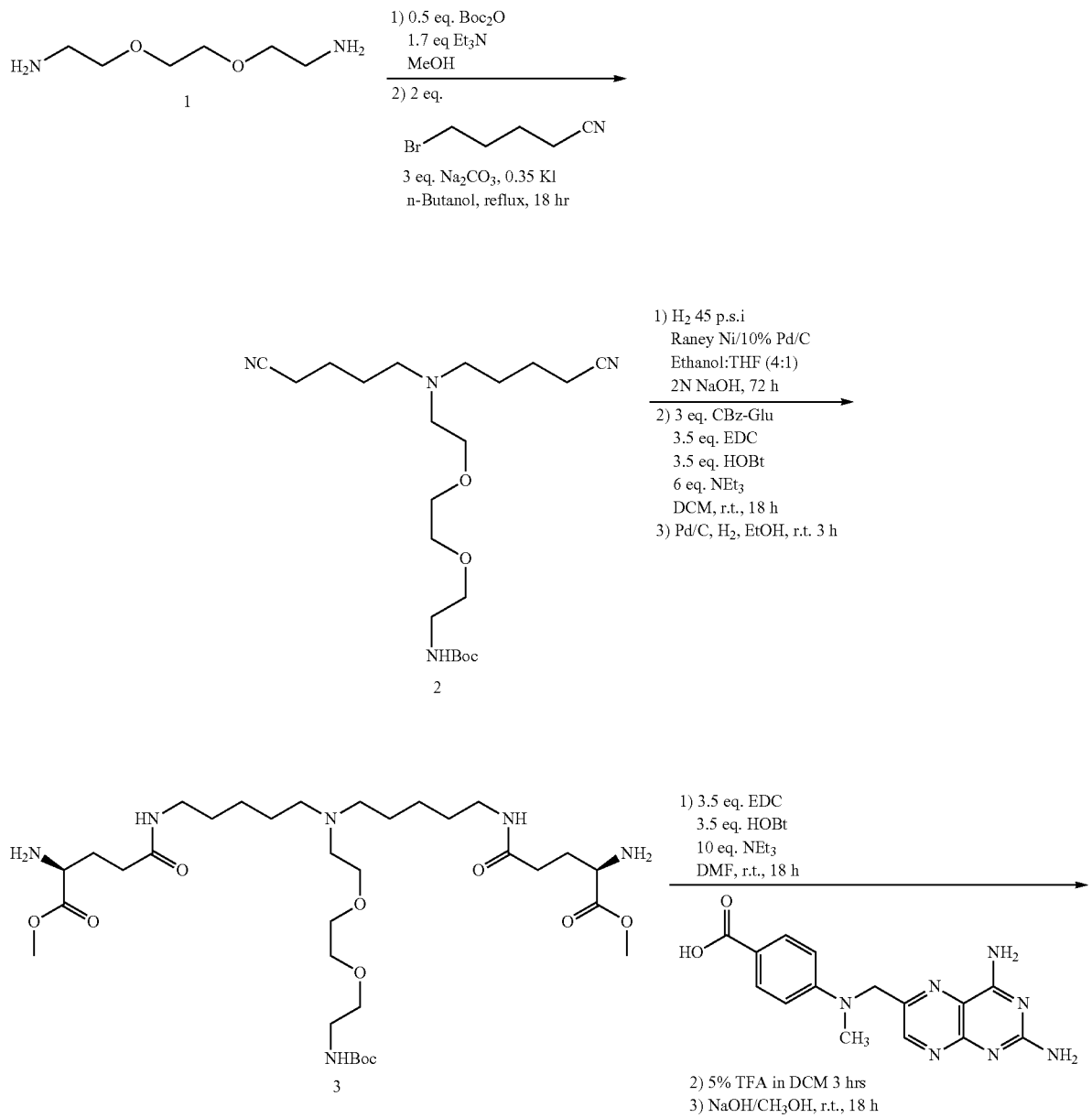

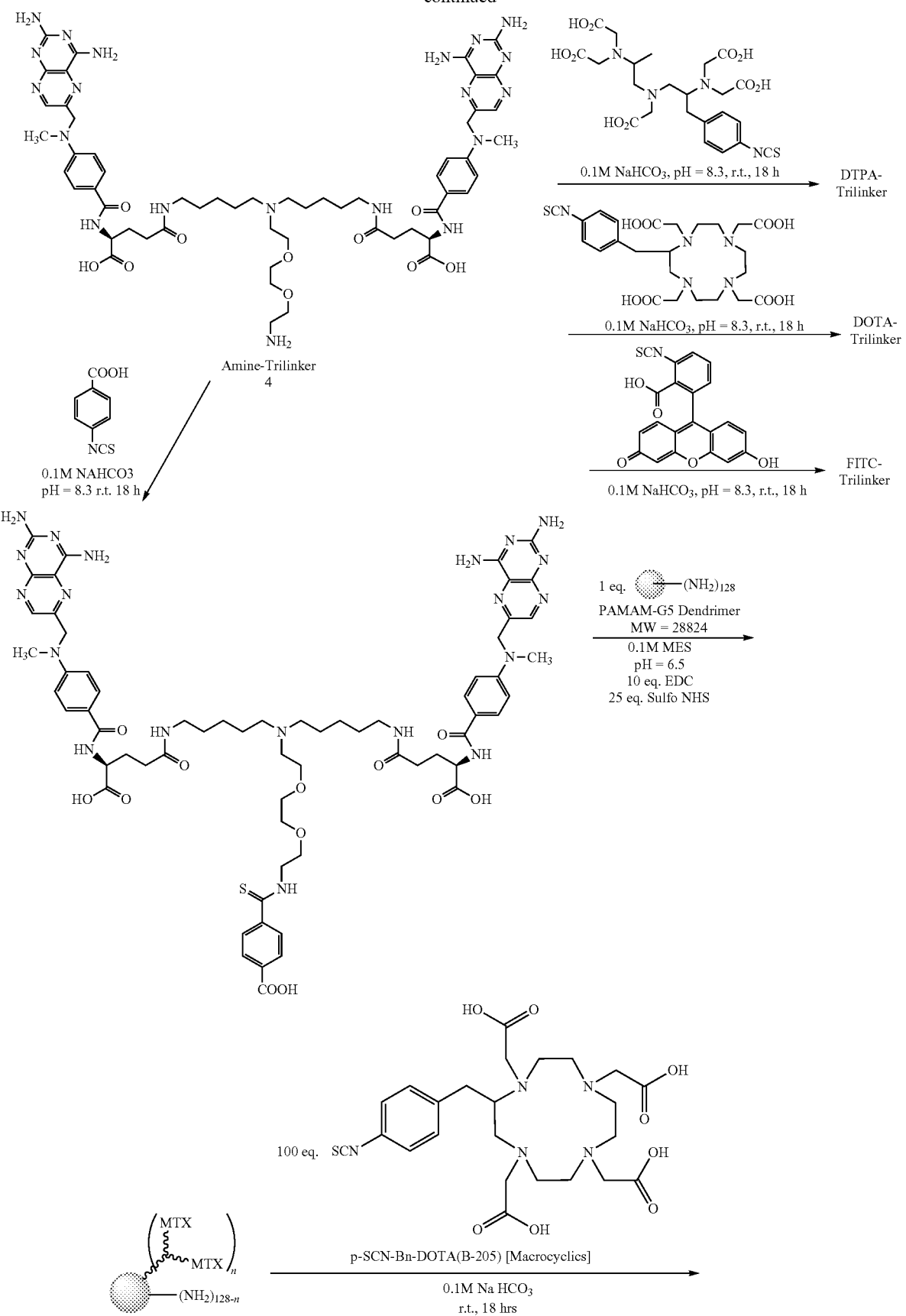

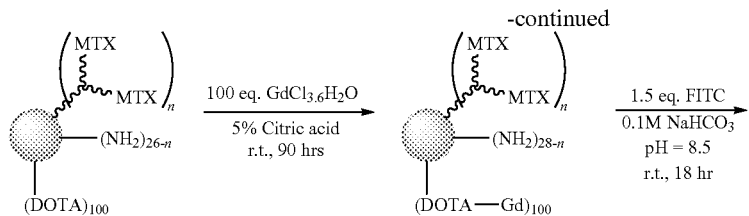
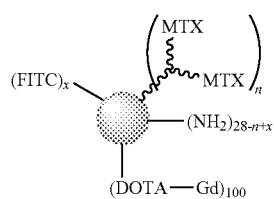

TABLE A

| Nanoparticle | $R_1$ (mM−1S−1) |
|---|---|
| MTXdendrimerNP | 19.6 |
| MTXdendrimerNP-DHFR$_2$-antiCD3 | 18.4 |
| MTXdendrimerNP-DHFR$_2$-antiCD22 | 17.3 |

T1 Relaxivities of Multifunctional Dendrimer

Example 2B Conjugation of DHFR-Fusion Proteins Nanoparticles

Functionalized gold nanoparticles (GNPs) have enormous potential in biomedical applications, such as diagnosis and therapy. (see, e.g., Dykman, L.; Khlebtsov, N. *Chem. Soc. Rev.* 2011; Giljohann, D. A.; Seferos, D. S.; Daniel, W. L.; Massich, M. D.; Patel, P. C.; Mirkin, C. A. *Angew. Chem. Int. Ed.* 2010, 49, 3280-94; and Sperling, R. A.; Rivera gil, P.; Zhang, F.; Zanella, M.; Parak, W. J. *Chem. Soc. Rev.* 2008, 37, 1896-1908) This would be especially the case if effective tumor-targeting molecules could be incorporated onto the surface of GNPs as the delivery of the functionalized GNPs to tumors would be maximized to afford effective diagnostic or therapeutic results. Single-chain antibodies (scFvs) are one of the effective targeting molecules that may be used to accomplish this goal. As described herein, targeted gold nanoparticles, utilizing the strong binding of DHFR-DHFR-scFv with bis-MTX, have been synthesized.

Two approaches for the conjugation of DHFR-DHFR-scFv to the GNPs are described herein. The first strategy includes incorporation of PEG-thiol and bis-MTX thiol derivatives onto the GNP surface followed by conjugation of DHFR-DHFR-scFv to the bis-MTX on the GNPs (Scheme B(a)). In the second approach, conjugation of bis-MTX with DHFR-DHFR-scFv is performed prior to incorporating the bis-MTX thiol derivative onto the GNP surface (Scheme B(b)).

Scheme B. Scheme for the bioconjugation of DHFR-DHFR-scFv to gold nanoparticles (a)

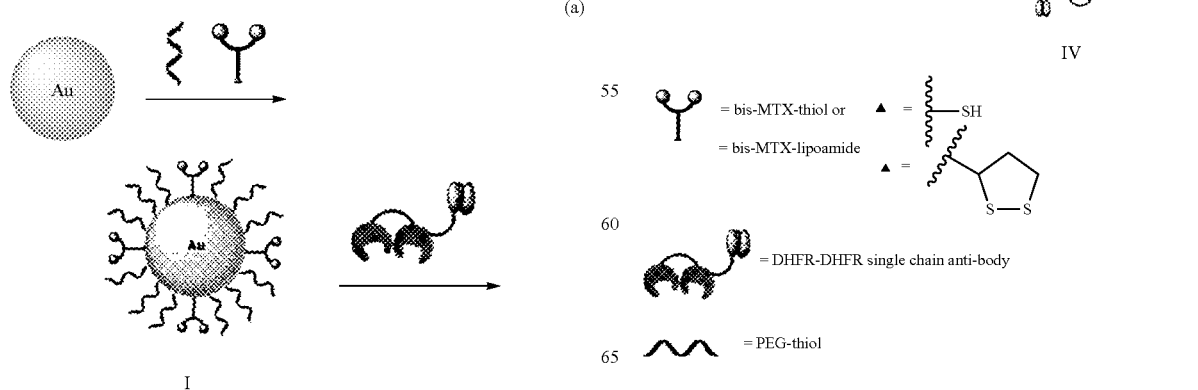

(b)

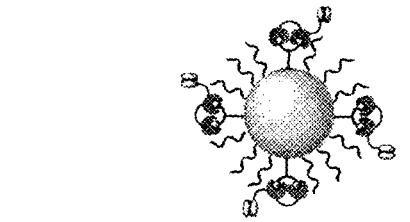
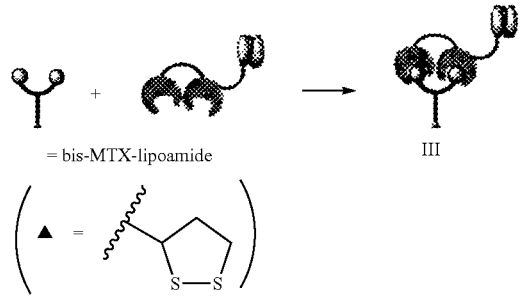
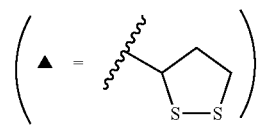
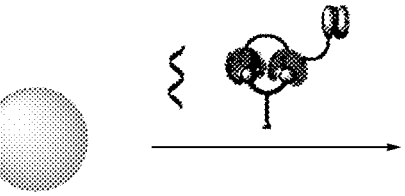
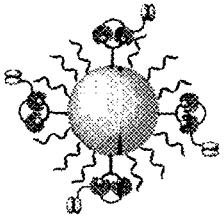
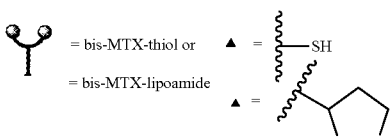

Figure 2:
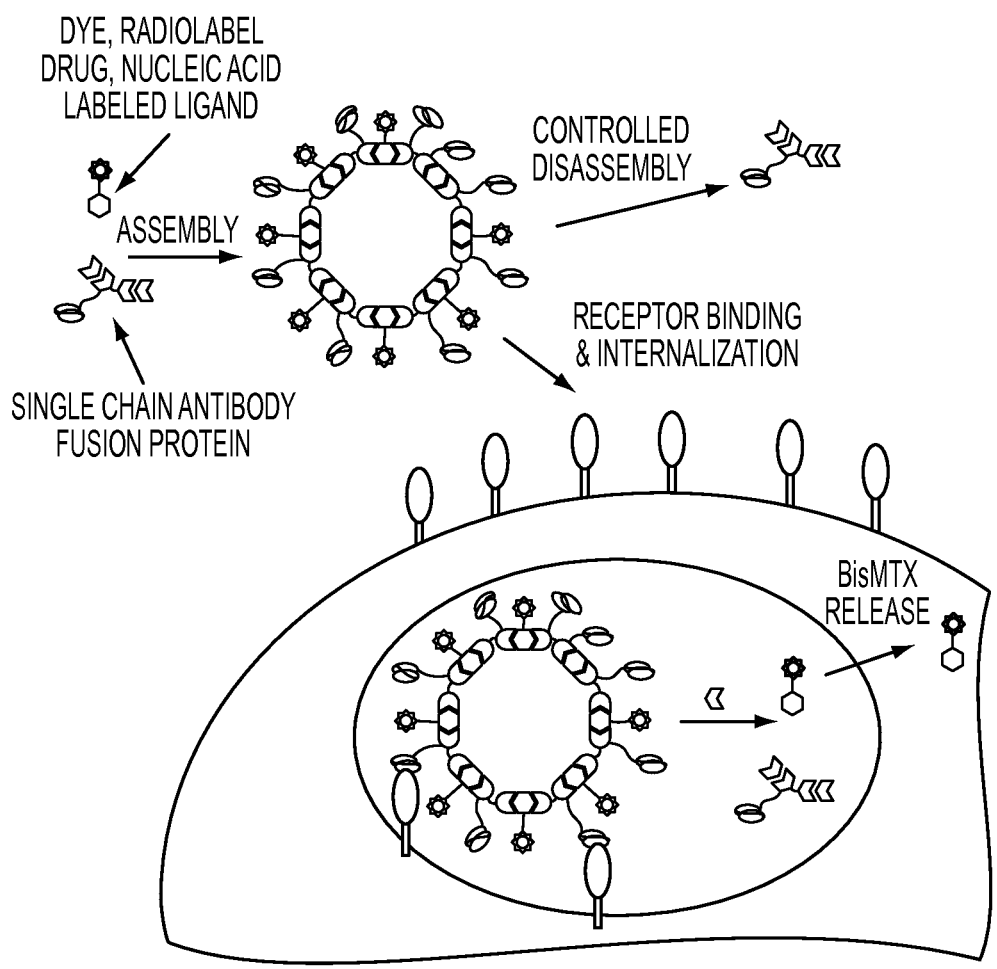
FIG. 2. Schematic showing the formation of CSAN with a branched bisMTX ligand, functionalized with a therapeutic or imaging agent. CSAN binding and endocytosis by cell surface receptors carries the cargo inside the cells where it can be released. CSANs can be disassembled by small molecule DHFR inhibitors.

Two bis-MTX-thiol derivatives, which have a thiol or lipoic acid moiety, have been designed and synthesized (Scheme C). Lipoic acid-conjugated bis-MTX compounds were prepared because cyclic disulfide bond in lipoic acid has a stronger affinity to GNPs than mono-thiol group and it is stable in aqueous solution. First, bis-MTX trilinker (2) was synthesized to introduce a thiol or lipoic acid group. The synthesis of bis-MTX trilinker (2) includes eight steps. In order to introduce thiol moieties, both bis-MTX trilinker precursor (1) and bis-MTX trilinker (2) were used. Using bis-MTX trilinker precursor (1) and thiol-dPEG4-acid, compound 3 was successfully obtained. Lipoic acid was also coupled to bis-MTX trilinker (2) to obtain compound 4 (FIG. 2). However, compound 4 has low solubility in water. Therefore, more water-soluble compound (5) was prepared using lipoamide-dPEG4-acid and bis-MTX trilinker precursor (1).

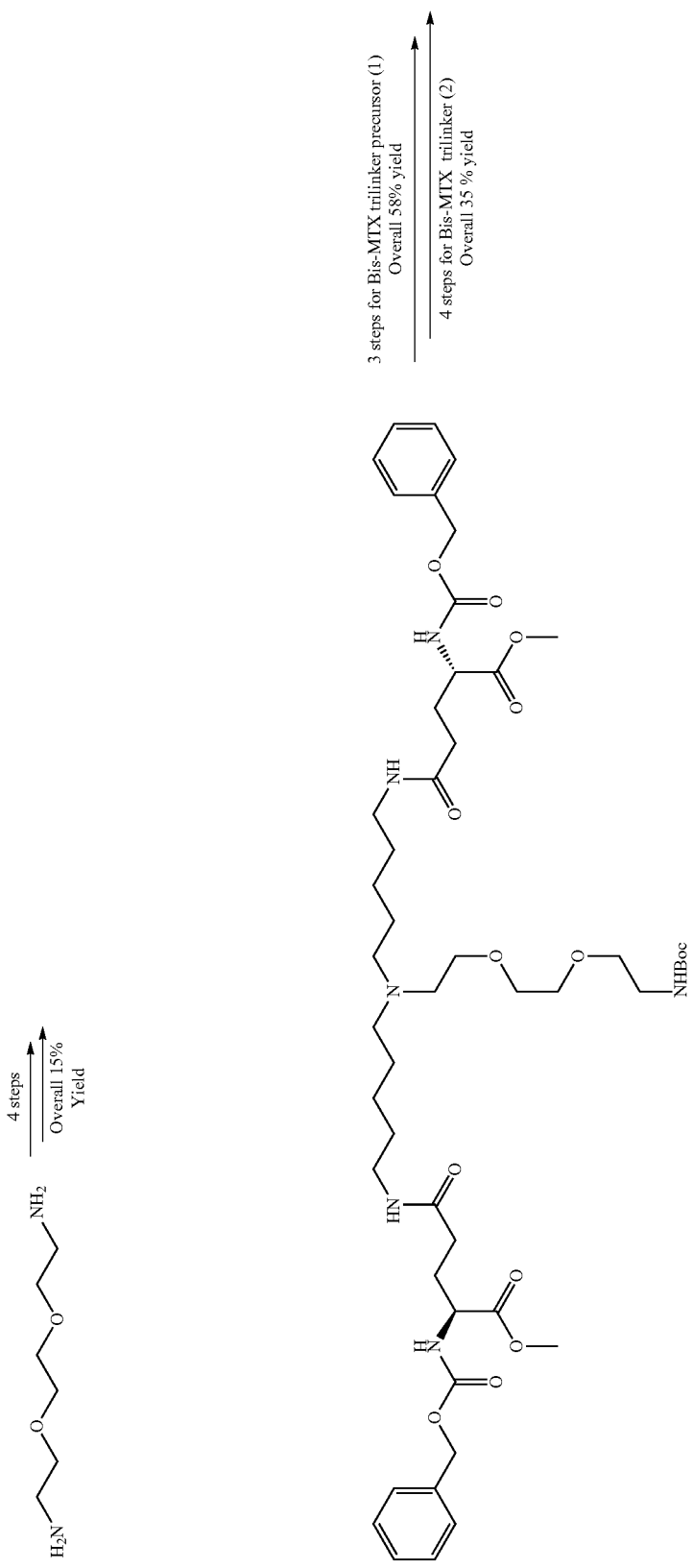

-continued
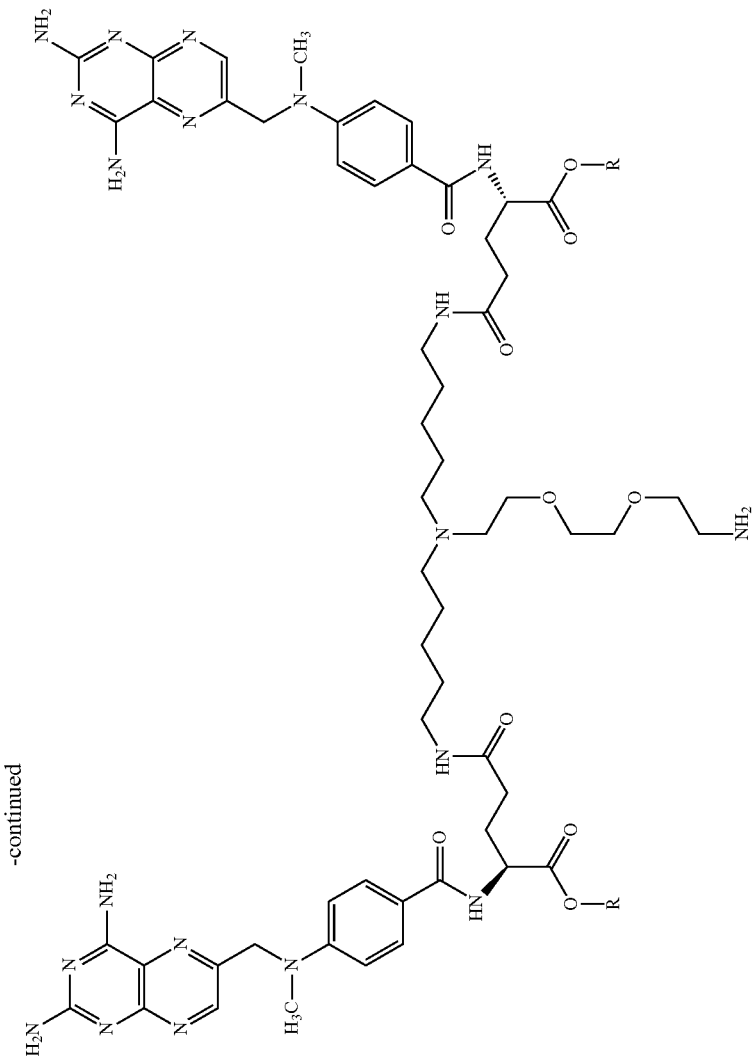
1 (R = CH3): Bis-MTX trilinker precursor
2 (R = H): Bis-MTX trilinker

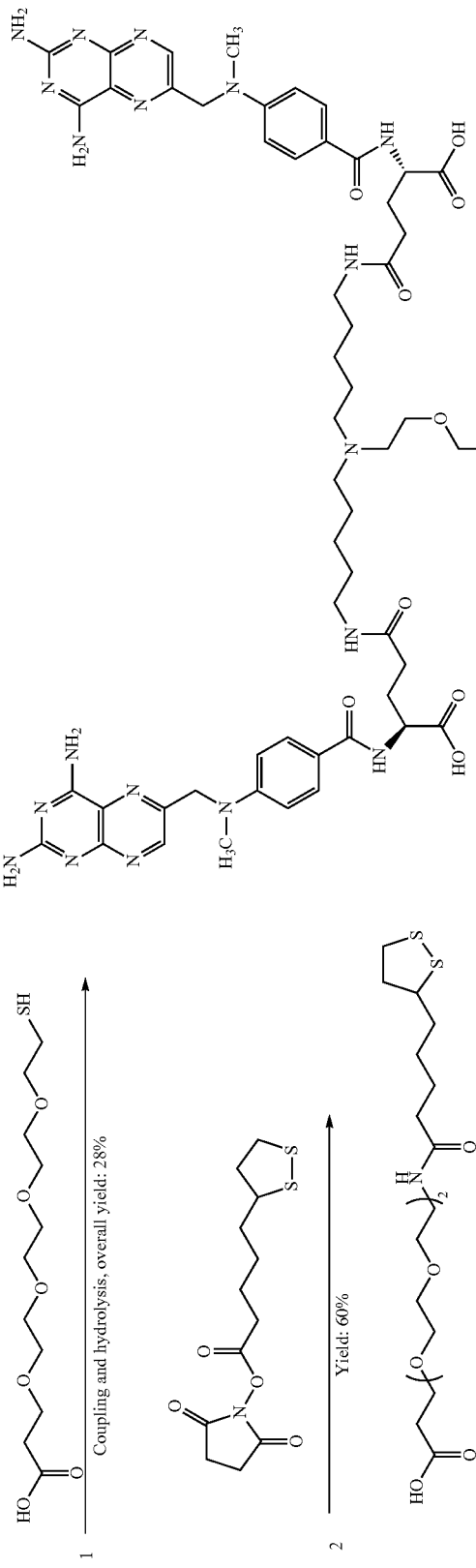
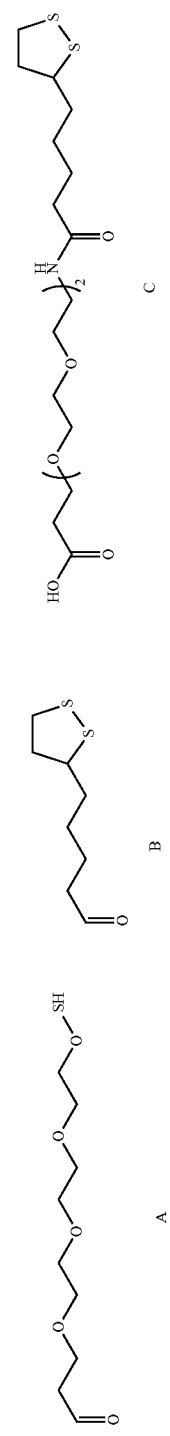

In addition to the synthesis of bis-MTX thiol derivatives, mono-MTX-thiol derivatives were also prepared for the comparison with the use of bis-MTX thiol derivatives (Scheme D). First, mono-MTX-linker precursor (6) was prepared in seven steps. Lipoamide-dPEG4-acid was then coupled to compound 6 to obtain compound 7. When thiol-dPEG4-acid was coupled to compound 6, both mono-MTX-thiol (8) and mono-MTX-thiol dimer (9) were obtained.

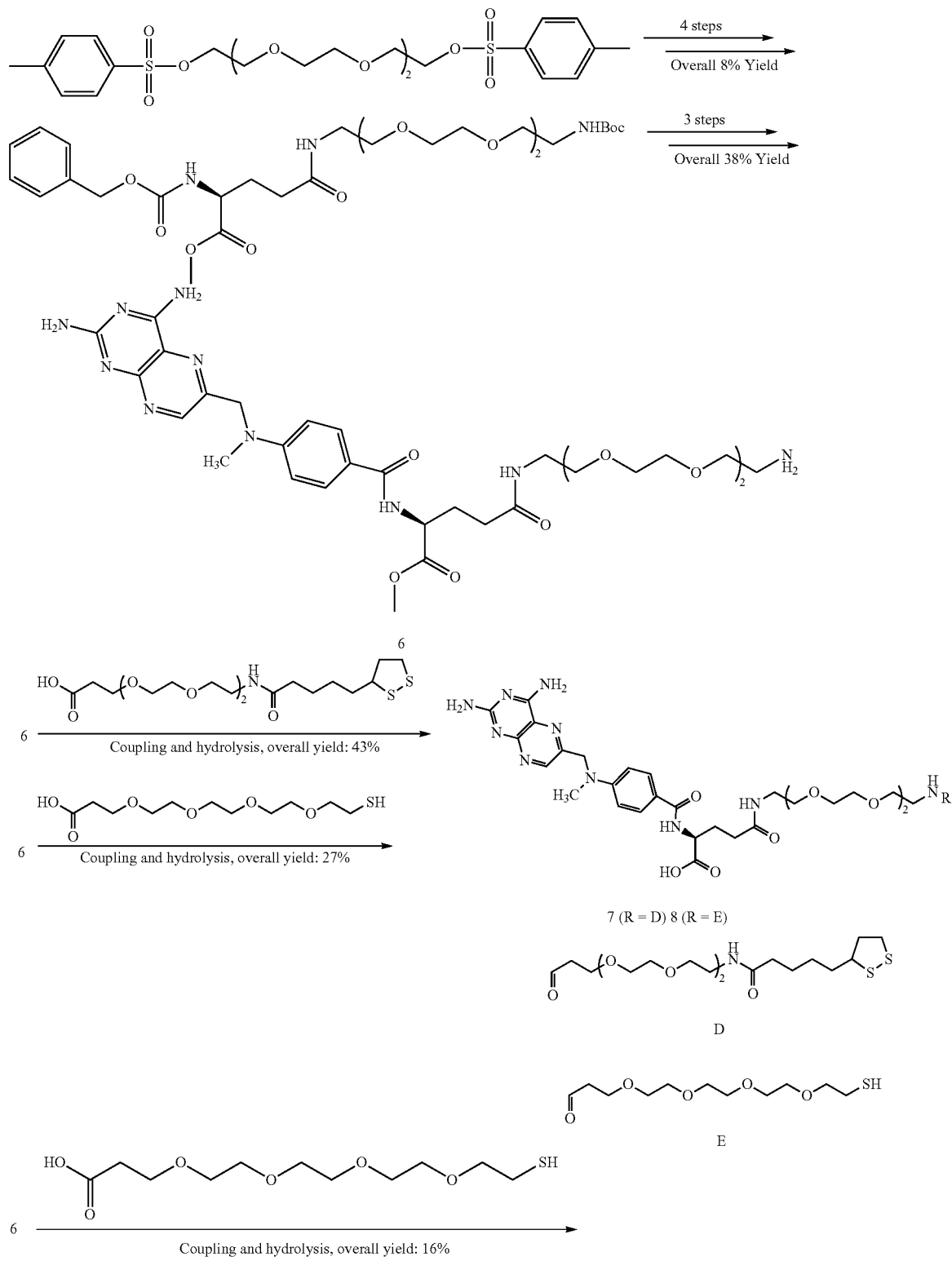

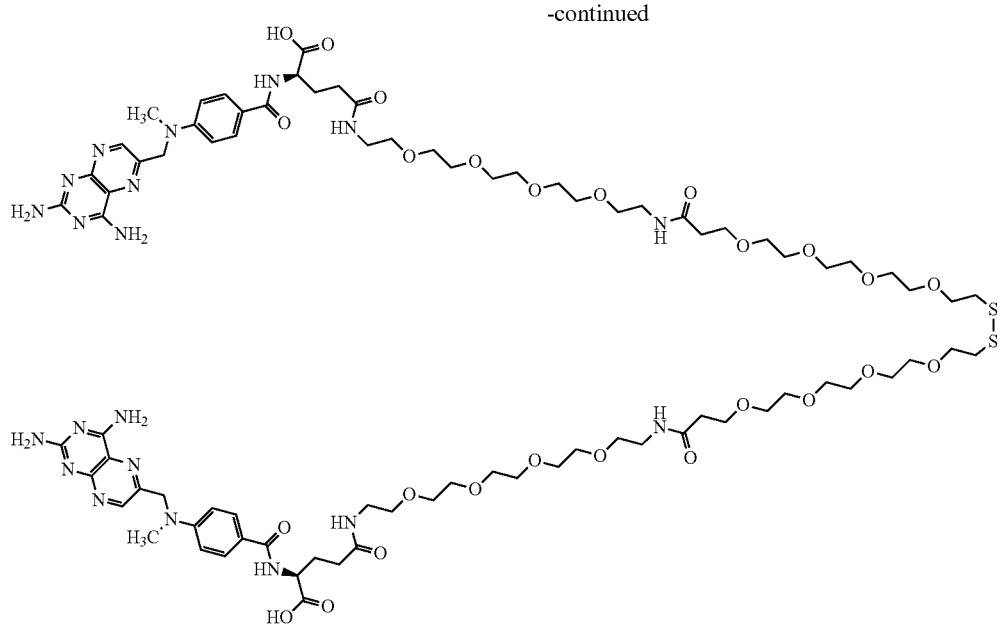

9

After obtaining bis-MTX-thiol derivatives, bis-MTX-thiol (3) was incorporated onto GNPs. First, the stability of mPEG-thiol (MW 2000)-conjugated GNPs was tested in 1% NaCl. (Chattopadhyay, N.; Cai, Z.; Pignol, J. P.; Keller, B.; Lechtman, E.; Bendayan, R.; Reilly, R. M. *Mol. Pharm.* 2010, 7, 2194-206.

Figure 3:
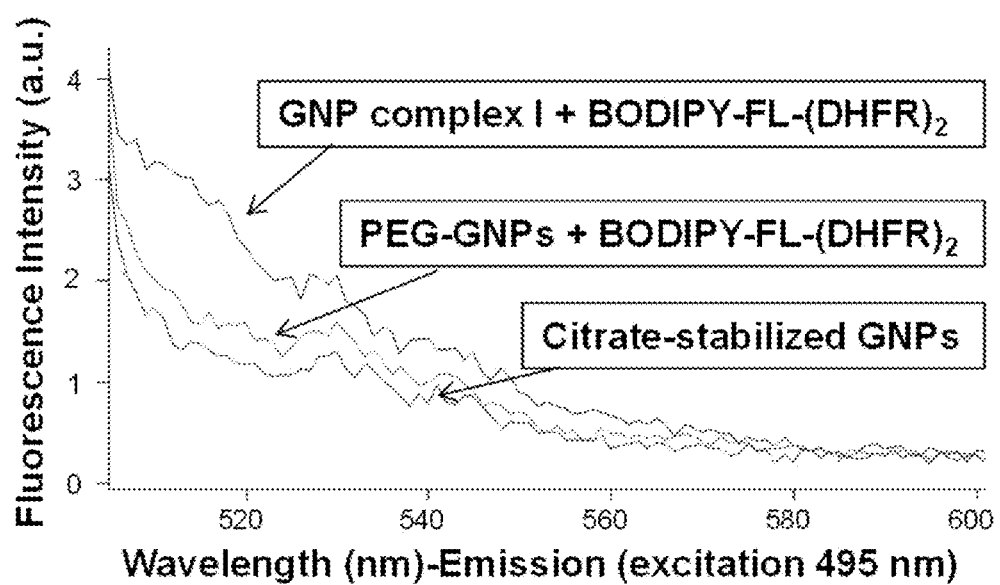
FIG. 3. Graph showing fluorescence of BODIPY-FL-(DHFR)$_2$-bound GNPs.
Figure 4:
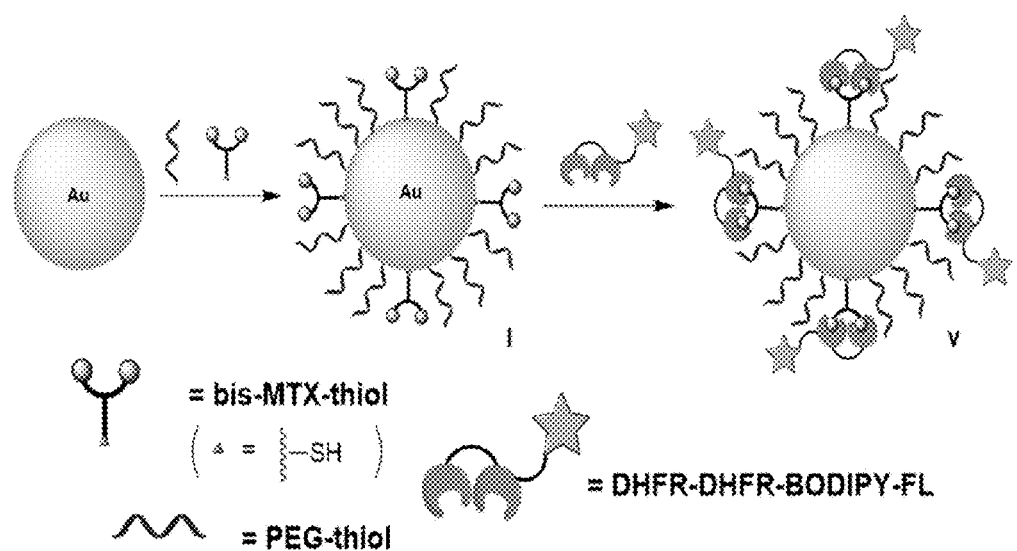
FIG. 4. Scheme for the bioconjungation of BODIPY-FL (DHFR)$_2$ on gold nanoparticles.

The result showed that 10000-fold molar excess of mPEG-thiol (MW 2000) is important for making stable GNPs. Then mPEG-thiol- and bis-MTX-thiol (3)-conjugated GNPs (GNP complex I, in Scheme B) were prepared. In the next step, conjugatation of $(DHFR)_2$ to the bis-MTX on the GNP complex I was attempted. Fluorophore (BO-DIPY-FL)-coupled $(DHFR)_2$ was used and the fluorescence of the resulting GNPs was measured FIG. 3 and FIG. 4). The experiment showed that that BODIPY-FL-$(DHFR)_2$ was bound to GNP complex I. However, some of BODIPY-FL-$(DHFR)_2$ was also bound to the GNPs nonspecifically.

For the second approach of the bioconjugation of DHFR-DHFR-scFv to gold nanoparticles (Scheme B(b)), synthesis of the bis-MTX-$(DHFR)_2$ complex was attempted (internal monomer) (Scheme F). Instead of using $(DHFR)_2$-scFv, DHFR-DHFR protein (having 13 amino acid inter-domain linker, called 13DD) was used as a test experiment. In addition, the dimer of mono-MTX-thiol (9, in Scheme D) was also incubated with 13DD to see if it forms an internal monomer. SEC experiment showed that both bis-MTX-lipoamide (5) and the dimer of mono-MTX-thiol (9) formed internal monomers with small amount of dimers (Scheme F).

Scheme F. Scheme for the formation of the internal monomers

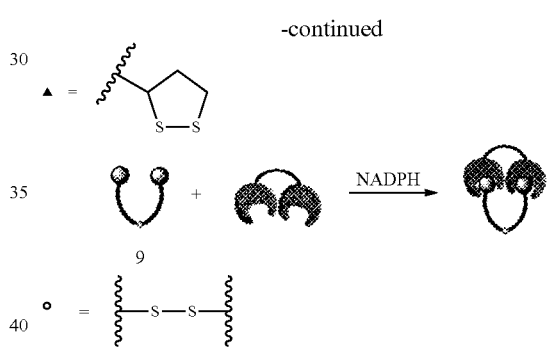

Therefore, both internal monomers in the second approach in Scheme B(b) can be used. Furthermore, since the dimer of mono-MTX-thiol (9) could form oligomers (at least dimer) with $(DHFR)_2$-scFv, the oligomer itself could be used as an anticancer drug if the disulfide bond of compound 9 is effectively cleaved inside the cancer cells.

The synthesis of mono- and bis-MTX-thiol derivatives has been completed and it has been observed that binding of DHFR-DHFR proteins to the bis-MTX on the GNPs occurs. In addition, bis-MTX-lipoamide (5) and mono-MTX-thiol dimer (9) form internal monomers with DHFR-DHFR proteins. Functionalized GNPs will be synthesized, and the level of internalization into tumor cells will be determined.

Example 3 Fusion Proteins for the Delivery of Oligonucleotides and Proteins

The advent and growth of antibody-drug conjugates (ADCs) has demonstrated the significant potential afforded targeted drug delivery. Drugs that have previously been abandoned from development pipelines due to extreme toxicities or undesirable pharmacokinetic properties have been resurrected for use as antibody conjugates, with targeted delivery bypassing their previous off target toxicities. Outside of the traditional medicinal chemistry development of therapeutic small molecule drugs, there has been continued interest in the therapeutic use of toxic proteins and oligonucleotides. These too have been developed as antibody conjugates, usually as fusion proteins or chemical conjugates, again allowing for their targeted delivery to cells of interest. Small molecules and oligonucleotides have also been conjugated to the catalytic antibody 38C2 to create chemically programmable antibodies. Changing the cytotoxic effector being delivered or the diversity of the targeting elements being utilized with these approaches requires re-engineering and development. As such, a simple system that to attain robust targeted cellular and tissue drug delivery is needed.

As described herein, it has been demonstrated that dihydrofolate reductase-single-chain variable fragment (scFv) fusion proteins can be used for the targeted cellular delivery of oligonucleotides, conjugated small molecules and proteins, via labeling of oligonucleotides by bis-methotrexate.

The advent and growth of antibody-drug conjugates (ADCs) has demonstrated the significant potential afforded targeted drug delivery. (Alley et al., Curr. Opin. Chem. Biol. 2010, 14, 529-537; Katz et al., Clin. Cancer Res. 2011, 17, 6428-36; Chari, Acc. Chem. Res. 2008, 41, 98-107) Drugs that have previously been abandoned from development pipelines due to extreme toxicities or undesirable pharmacokinetic properties have been resurrected for use as antibody conjugates, with targeted delivery bypassing their previous off target toxicities. Outside of the traditional medicinal chemistry development of therapeutic small molecule drugs, there has been continued interest in the therapeutic use of toxic proteins and oligonucleotides. These too have been developed as antibody conjugates, usually as fusion proteins or chemical conjugates, again allowing for their targeted delivery to cells of interest. (Oh et al., Clin. Cancer Res. 2009, 15, 6137-6147; Mathew et al., Cancer Sci. 2009, 100, 1359-1365; Choudhary et al., Drug Discover. Today 2011, 16, 495-503) Small molecules and oligonucleotides have also been conjugated to the catalytic antibody 38C2 to create chemically programmable antibodies. (Rader et al., Proc. Natl. Acad. Sci. USA 2003, 100, 5396-5400; Gavrilyuk et al., ChemBioChem 2010, 11, 2113-2118; Wuellner et al., Angew. Chem. Int. Ed., 2010, 49, 5934-5937) Changing the cytotoxic effector being delivered or the diversity of the targeting elements being utilized with these approaches requires re-engineering and development. Hence, it would be beneficial to develop a simple system that would require minimal redesign to attain robust targeted cellular and tissue drug delivery.

The formation of chemically self-assembled antibody nanorings (CSANs) has been reported by oligomerizing antiCD3 single chain variable fragment (scFv) containing dimeric dihydrofolate reductase fusion proteins (DHFR$^2$antiCD3) with a bis-methotrexate (bis-MTX) ligand. (Li et al., Chem. Int. Ed., 2008, 47, 10179-10182; Li et al., J. Am. Chem. Soc. 2010, 132, 17247-17257) The antiCD3 CSANs interact with CD3+ T cells in a tissue specific manner similar to that of the parental antiCD3 monoclonal antibody. As described herein, it has been proposed that DHFR$^2$antiCD3 proteins could be used to carry single stranded oligonucleotides and DNA duplexes, with attached cargoes, inside cells via modification of bis-MTX (Schemes 1.1a and 1.2a).

A bis-MTX molecule has been prepared with a third arm containing a maleimide for reaction with thiol functionalized oligonucleotides. In order to study the uptake of bis-MTX oligo conjugates by cells, a bis-MTX oligo conjugate labelled with fluorescein (bis-MTX oligo FITC) was prepared. Bis-MTX oligo conjugates were also analyzed and characterized by LCMS.

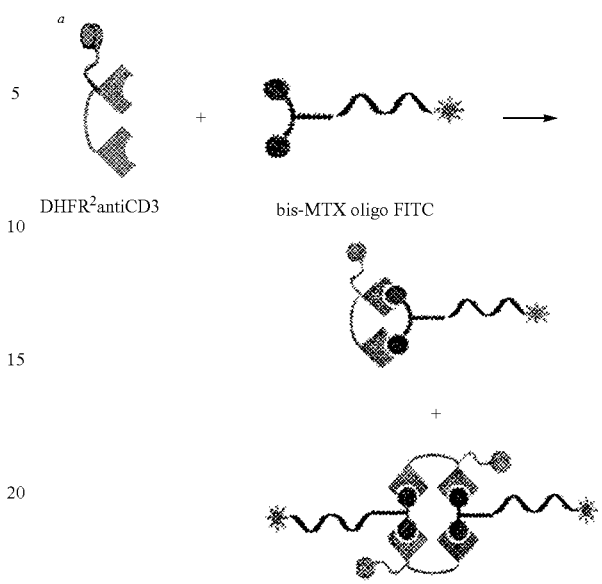

DHFR$^2$antiCD3    bis-MTX oligo FITC

Self-assembly of monomeric and dimeric antiCD3-oligonucleotide conjugates through DHFR-MTX binding was demonstrated. DHFR$^2$antiCD3 contains two DHFR proteins and an antiCD3 scFv. Bis-MTX oligo FITC has bisMTX, attached to the oligo, which is labeled with FITC. FITC labeled oligonucleotides were delivered to HPB-MLT cells via antiCD3 scFv at 37 and 4° C.

Incubation of bis-MTX oligo FITC with DHFR$^2$antiCD3, which has a 13 amino acid linker between the DHFR proteins, results in a mixture of dimeric and internal monomeric antiCD3 nanorings as analyzed by size exclusion chromatography. DHFR$^2$antiCD3 (68 kDa) elutes as a single peak with a retention time of 32.7 min. Upon incubation with bis-MTX oligo FITC, this peak disappears and two new prominent peaks appear, at 27.5 min and 30.6 min. Both of these peaks show absorbance at 494 nm, revealing the presence of FITC labeled oligonucleotide in the eluted species. The elution profile is similar to that obtained when bis-MTX is incubated with DHFR$^2$antiCD3, although there appears to be a shift towards more internal monomer when bis-MTX oligo FITC is used for the dimerization. When DHFR$^2$antiCD3 is incubated with bis-MTX the internally cyclized DHFR$^2$antiCD3 peak elutes slightly later than DHFR$^2$antiCD3, due to the decreased hydrodynamic radius of the species. Here the internal monomeric species is larger than DHFR$^2$antiCD3 alone as bis-MTX oligo FITC is of higher molecular weight and will have a greater hydrodynamic radius as compared to bis-MTX.

Bis-MTX oligo FITC and DHFR$^2$antiCD3 were incubated with CD3+ HPB-MLT (T-leukemia) cells and after washing the cells were analyzed by flow cytometry. Cells treated with antiCD3-oligo-FITC showed increased fluorescence intensity, as compared to untreated cells, suggesting interaction between the FITC labelled oligo and CD3+ cells. Incubation with bis-MTX oligo FITC, in the absence of DHFR$^2$antiCD3, showed only a small increase in fluorescence, presumably due to non-specific binding, demonstrating the necessity of antiCD3 scFv for the interaction of the oligonucleotide with the cells. Pre-incubation of HPB-MLT cells with the parental antiCD3 monoclonal antibody (mAb; UCHT-1) prevented binding of Bis-MTX oligo FITC and DHFR$^2$antiCD3, as indicated by no increase in fluorescence showing the specific interaction between the construct and cell-surface CD3. The cell surface specific nature of binding was further confirmed by incubation of HPB-MLT cells with varying concentrations of construct. The observed fluorescence, as measured by flow cytometry, decreased with decreasing concentration of fluorescently labeled species. Incubation of Bis-MTX oligo FITC and DHFR²antiCD3 with CD3 negative Raji cells (B cells) resulted in only minor non-specific binding, showing cell specificity.

To further probe the cellular interaction, bis-MTX oligo FITC and DHFR²antiCD3 was incubated with HPB-MLT cells, at either 4 or 37° C. after which the cells were imaged by fluorescence confocal and differential inference contrast microscopy. Green fluorescent punctates were observed inside cells treated with antiCD3-oligo-FITC at 37° C.; thus indicating that the bis-MTX oligo FITC has been endocytosed along with DHFR²antiCD3. A similar image with green fluorescent punctates is obtained upon incubation of FITC labeled UCHT-1 with HPB-MLT. Cells treated at 4° C. show green fluorescence on the cell surface suggesting that at this temperature DHFR²antiCD3, with bis-MTX oligo FITC, binds to the CD3 receptor on the cell membrane but is not internalized. The temperature dependence of internalization indicates that endocytosis occurs via an energy dependent mechanism, which is consistent with the internalization of CD3. Co-localization studies at 37° C. with transferrin, a marker of receptor-mediated endocytosis, suggested that DHFR²antiCD3, with bis-MTX oligo FITC localize to endosomes, in a similar manner to UCHT-1. This also suggests that the construct follows an internalization mechanism similar to transferrin, which relies on clathrin-dependent endocytosis. (Hanover et al., J. Biol. Chem. 1985, 260, 5938-5945) Incubation of bis-MTX oligo FITC with HPB-MLT cells, in the absence of DHFR²antiCD3, results in no increased cellular fluorescence, thereby demonstrating the necessity of the scFv-receptor interaction for oligonucleotide binding and uptake.

Having shown the ability of DHFR²antiCD3 to carry bis-MTX functionalized single stranded oligonucleotides inside T-leukemia cells, the capability of the antiCD3-oligo conjugates to deliver cargoes inside cells through the formation of double stranded helices was explored. In order to reduce the heterogeneity of the species formed, DHFR²antiCD3 was pre-incubated with NADPH prior to addition of the bis-MTX oligo. This results in formation of only the intramolecular dimer species as analyzed by SEC. NADPH enhances the affinity of MTX for DHFR by at least 100-fold, thus favouring intramolecular dimerization. (Kamen et al., Biochem. Pharmacol. 1983, 32, 1837-1841) This can be seen by the decrease in the absorbance of the peak eluting at 27.5 min and a concomitant increase in the peak eluting at 30.6 min, as compared to the elution profile when the species are mixed in the absence of NADPH. Pre-incubation with NADPH has a similar effect on the elution profile when the protein is mixed with bis-MTX.

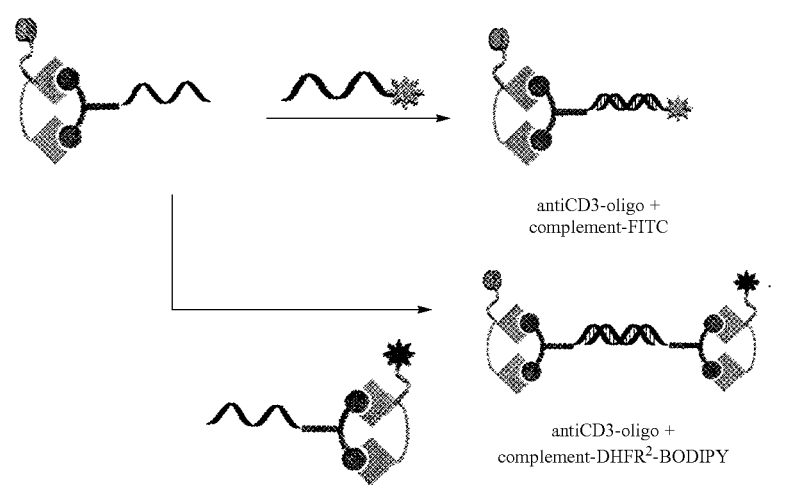

AntiCD3-oligo is formed from DHFR²antiCD3 and bis-MTX oligo. Incubation with either complement-FITC (top arrow) or complement-DHFR²-BODIPY (bottom arrow) results in duplex formation between the complementary oligos yielding the final constructs. Fluorescence confocal and differential interference contrast and overlay images of complement-FITC and complement-DHFR²-BODIPY delivered to HPB-MLT cells via duplex formation with DHFR²antiCD3-oligo at 37° C. have been created.

To evaluate the use of duplex formation for the delivery of small molecules (e.g., drugs, dyes, etc), a FITC labelled oligonucleotide was used to allow the use of flow cytometry and confocal microscopy to visualize delivery. However, this time bis-MTX was conjugated to an oligonucleotide that is complementary to the FITC labelled oligonucleotide. The bis-MTX oligo was incubated with DHFR²antiCD3, in the presence of NADPH, to form the intramolecular species. To this mixture was added the complementary FITC labelled oligonucleotide, thus allowing sequence specific DNA duplex formation. For the delivery of proteins, both complementary strands at the 3' end were conjugated with bis-MTX. One strand was then conjugated to DHFR²antiCD3 in the presence of NADPH. In a similar manner, the other strand was incubated in the presence of NADPH with a DHFR² quadruple mutant (C85A/C152S/C257A/C324S) containing a C-terminal Gly-Gly-Cys tag that has been site specifically labelled with the maleimide BODIPY-FL fluorescent dye (DHFR²-BODIPY). The two intramolecular dimers, with complementary oligos, were incubated at 4° C. overnight allowing for duplex formation. The DHFR²antiCD3-duplex FITC and DHFR²antiCD3-duplex DHFR²-BODIPY conjugates were then incubated with HPB-MLT cells and analyzed by flow cytometry and confocal microscopy Flow cytometry analysis of HPB-MLT cells incubated with DHFR²antiCD3-duplex FITC revealed an increase in fluorescence as compared to the unlabelled cells. Similarly, cells treated with the DHFR²antiCD3-duplex DHFR²-BODIPY showed an increase in fluorescence, while only a small increase in fluorescence and hence only minimal non-specific interactions with the HPB-MLT cells were observed for cells treated with DHFR²-BODIPY alone. Neither of the constructs showed specific binding to the CD3 negative Raji cells. Unlabeled UCHT-1 (antiCD3 mAb) was able to prevent binding of both fluorescently labeled constructs, as observed by minimal increases in fluorescence as compared to the unstained cells. Both constructs also show concentration dependence of the observed fluorescence when incubated with HPB-MLT cells, in a similar manner to DHFR²antiCD3 with bis-MTX oligo FITC.

Fluorescence confocal microscopy demonstrated that cells treated with DHFR²antiCD3-oligo+complement-FITC and DHFR²antiCD3-oligo+complement DHFR²-BODIPY at 37° C. have internalized green punctates indicating binding and uptake of the labeled oligonucleotide and protein. Again, only cell surface binding was observed for cells treated with the conjugates at 4° C. Thus, the DHFR²—BisMTX based chemical self-assembled antibody-oligonucleotide conjugates affords a unique system for the programmable assembly and cellular delivery of oligonucleotides, drug conjugated oligonucleotides or DHFR² fusion proteins.

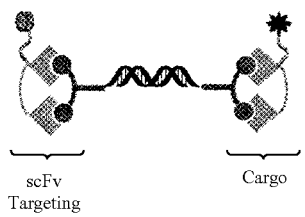

scFv Targeting    Cargo

Abbreviations
ADC, antibody drug conjugate; CSAN, chemically self-assembled antibody nanoring; DHFR, dihydrofolate reductase; FITC, Fluorescein isothiocyanate; LCMS, liquid chromatography mass spectrometry; MTX, methotrexate; SEC, size exclusion chromatography.

General Methods:
1. HPLC—Beckman Coulter with UV Detector
2. SEC-HPLC—Beckman Coulter with UV Detector
3. LC-ESI-Mass Spectrometry—Agilent MSD SL Ion Trap (1100 Series)
4. NMR—Varian MR 400 MHz NMR spectrometer Scheme 1.S1: Synthesis of Bis-MTX-Maleimide

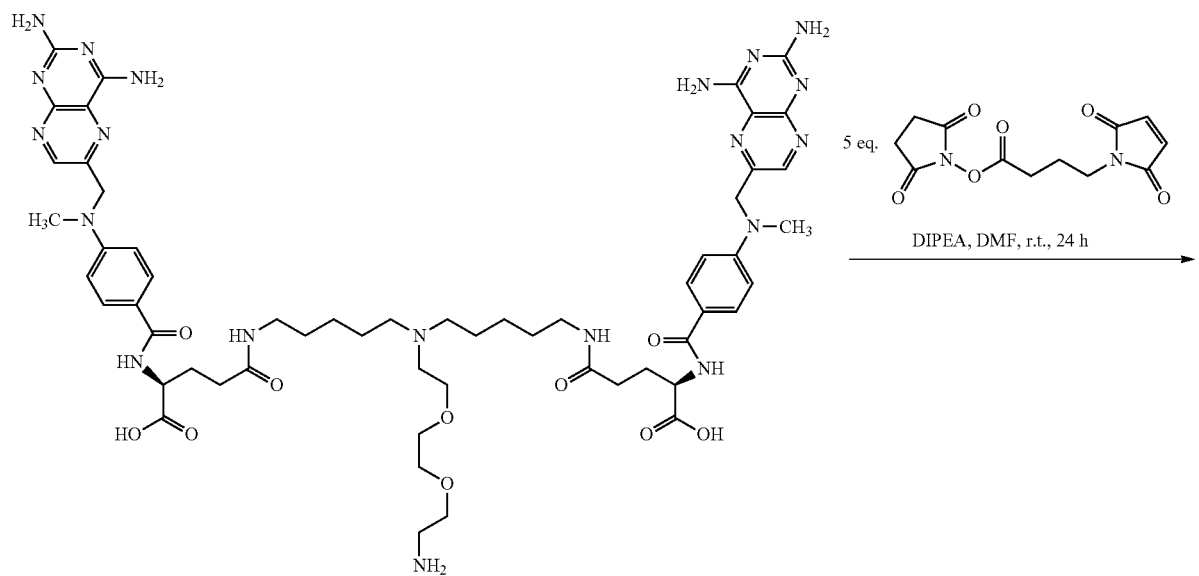

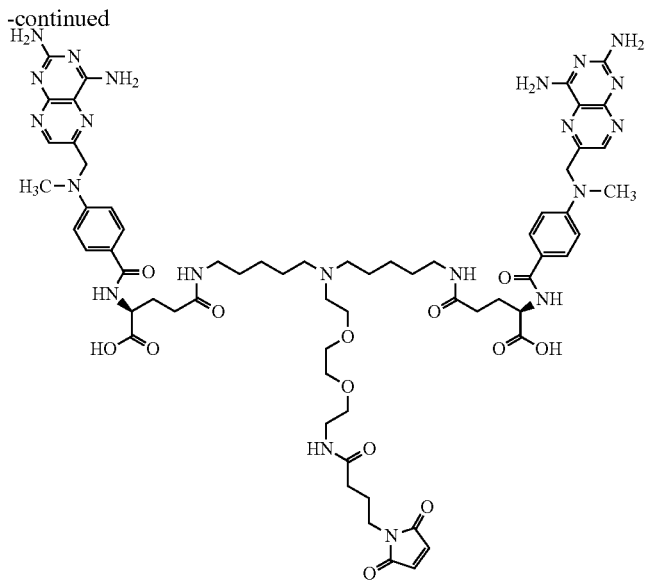

N-Succinimidyl 4-maleimidobutyrate was synthesized by previously reported method in literature. (Rich, D. H.; Gesellchen, P. D.; Tong, A.; Cheung, A.; Buckner, C. K. J. Med. Chem. 1975, 18, 1004-1010; Bidwell, G. L.; Fokt, I.; Priebe, W.; Raucher, D. Biochem. Pharmacol. 2007, 73, 620-631) The synthesis of Bis-MTX-NH$_2$ will be reported elsewhere. Bis-MTX-NH$_2$ was mixed with 5 eq of N-succinimidyl 4-maleimidobutyrate and 1 eq of N,N,-diisopropylethylamine (DIPEA) in dimethyl formamide (DMF) and stirred at room temperature overnight. The product was then purified by HPLC using 0.1% TFA in water (solvent A) and 0.1% TFA in acetonitrile (solvent B) on Haisil 100° A C8 RP column (5 μm, 250×10 mm, Haggins Analytical Inc). Product peak was isolated using a gradient of 2% to 50% B in 30 min and then to 100% in 5 min. Relevant fractions were pooled and lyophilized prior to storage (yield 1.5 mg, 75%) Bis-MTX-Maleimide was characterized by $^1$H NMR and ESI mass spectrometry.

$^1$H NMR (400 MHz, CD$_3$OD): δ 8.55 (s, 2H), δ 7.67 (d, 4H, J=8.8 Hz), δ 6.77 (d, 4H, J=8.8 Hz), δ 6.68 (s, 2H), δ 4.82 (s, 4H), δ 4.44 (m, 2H), δ 3.70 (t, 2H), δ 3.53 (m, 4H), δ 3.41 (m, 4H), δ 3.24 (m, 4H), δ 3.17 (s, 6H), δ 3.07 (m, 6H), δ 2.27 (t, 4H), δ 2.19 (m, 2H), δ 2.07 (t, 2H), δ 1.98 (m, 4H), δ 1.74 (m, 2H), 1.62 (m, 4H), 1.45 (m, 4H), 1.28 (m, 4H). ESI-MS—Low resolution: calculated for [(M+H)$^+$] C$_{64}$H$_{86}$N$_{21}$O$_{13}$: 1356.7. Found 1356.9. High resolution calculated for [(M+2H)$^{2+}$/2] C$_{64}$H$_{87}$N$_{21}$O$_{13}^{2+}$: 678.8391 found: 678.8401.

Scheme 1.S3: Synthesis of Bis-MTX Oligonucleotide

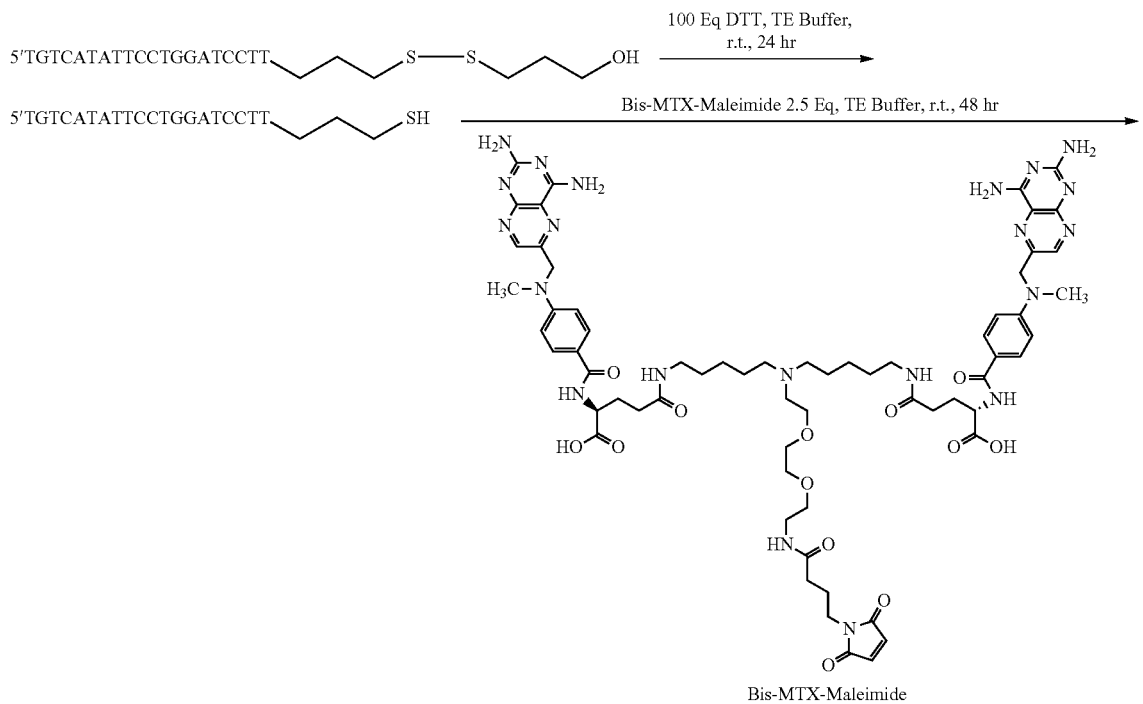

Bis-MTX-Maleimide

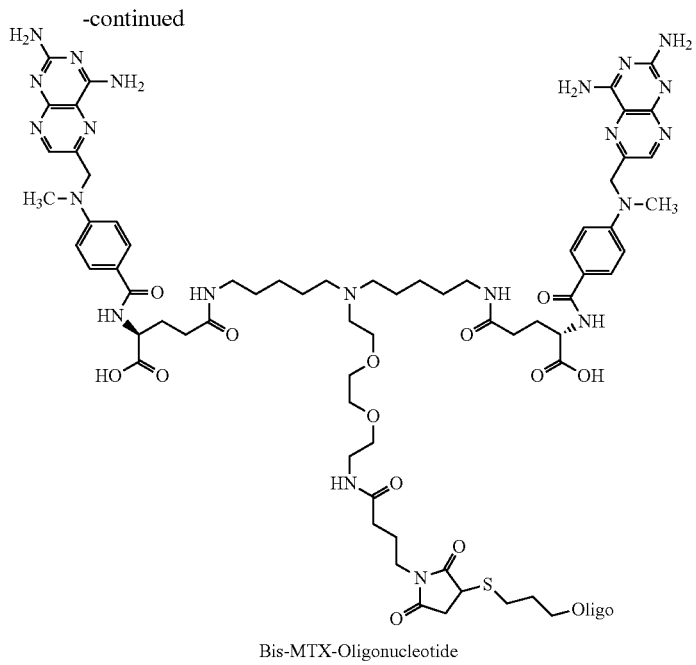

Bis-MTX-Oligonucleotide

Thiol protected oligonucleotides were purchased from IDT (Integrated DNA Technologies) and deprotected by 100 equivalent dithiothreitol (DTT) in TE Buffer (Tris 10 mM, EDTA 1 mM, pH 7.5) for 24 hr. DTT was removed by eluting the oligonucleotides through G25 spin columns (GE Healthcare Lifescience). Thiolated oligo were then magnetically stirred with 2.5 eq of Bis-MTX-maleimide in TE buffer for 48 hr at room temperature. Excess Bis-MTX-maleimide was then removed by centrifugation using an amicon (3 kDa MWCO, 7× with TE Buffer). Conjugates were analyzed by LC-ESI-MS.

Scheme 1.S4: LC-ESI-MS analysis of Bis-MTX Oligonucleotide

Completion of reaction and formation of products were evaluated by LC-ESI-MS. For LC, Zorbax SB-C 18 column (150 mm×0.5 mm, 5 μm, Agilent Technologies, Inc.) was used. The reaction mixture was eluted with 15 mM ammonium acetate (pH 6.6) (A) and 100% acetonitrile (B) with gradient of 2% B to 75% B over 35 min. Results for Bis-MTX-Oligo-Fluorescein (5' Fluorescein-TGTCATAT-TCCTGGATCC-Bis-MTX 3')-m/z=7488, Bis-MTX-Oligo (5' TGTCATATTCCTGGATCCTT-Bis-MTX 3')-m/z=7559, Bis-MTX-Compliment-Oligo (5' GGATCCAGGAATAT-GACA-Bis-MTX 3')-m/z=7066 were obtained.

Cell Culture:

HPB-MLT (T leukemia) and Raji (B lymphoma) cells were cultured in RPMI-1640 media (Lonza) supplemented with 10% (v/v) fetal bovine serum, L-Glutamine (2 mM final concentration), penicillin (100 units/mL), and streptomycin (100 μg/mL) in a humidified incubator with 5% $CO_2$ at 37° C.

$DHFR^2$-BODIPY-FL Labeling:

A plasmid encoding a quadruple mutant (C85A/C152S/C257A/C324S) DHFR-DHFR fusion protein with a 13 amino acid linker (GLGGGGGLVPRGT) between the DHFR proteins was prepared via plasmid mutagenesis. Starting from the plasmid encoding two cysteine free DHFR proteins linked by a 13 amino acid chain, a Glycine-Glycine-Cysteine (GGC) tag was added before the stop codon using QuikChange® Site-Directed Mutagenesis kit (Stratagene). The primers used were forward: 5'-C GAG CGT CGT GGA GGA TGC TAA TTA ATT AAT TCA C (SEQ ID NO:1) and reverse 5'-GTGAATTAATTAATTAGCATCCTCCAC-GACGCTCG (SEQ ID NO:2). The $DHFR^2$-GGC protein was expressed as described previously. (Carlson et al., J. Am. Chem. Soc. 2006, 128, 7630-7638.)

$DHFR^2$ was labeled with BODIPY-FL (Invitrogen) via cysteine-maleimide linkage, using a modification of a literature procedure. (Kim et al., Bioconjug. Chem. 2008, 19, 786-791.) $DHFR^2$ was first reduced with 100 eq. dithiothreitol (DTT) for 2 hr at 4° C. Then $DHFR^2$ was precipitated with 90% (w/v) ammonium sulfate by stirring at 4° C. for 1 hr. Protein slurry was spun down at 13000×g for 5 min at 4° C. Pellet was washed two times with P500 buffer (0.5 M NaCl, 50 mM $KH_2PO_4$, 1 mM EDTA, pH=7) containing 90% ammonium sulfate. Washed protein pellet was resuspended in P500 buffer containing 10 eq of BODIPY-FL maleimide dye (Invitrogen) and stirred at room temperature for 1 hr. After 1 hr, the reaction was quenched with 1 mM DTT. The labeled protein was further purified by SEC (size exclusion chromatography) using G75/G200 Superdex (GE Healthcare Lifesciences) column. More than 95% protein labeling was achieved as determined by UV-vis spectroscopy.

Confocal Microscopy:

$0.5\times10^6$ HPB-MLT cells were treated with FITC or BODIPY labeled constructs (1 μM) at either 4 or 37° C. for 1 hr in RPMI media. Cells were then pelleted by centrifugation (400×g, 5 min) After being washed twice with PBS (phosphate buffer saline) cells were incubated on Poly-Prep slides coated with poly-L-Lysine (Sigma) at 4 or 37° C. for 30 mins. Cells were then fixed with 4% paraformaldehyde solution for 10 mins and washed thrice with PBS. Finally, cells were treated with ProLong Gold Antifade reagent with DAPI (Invitrogen), a cover slip was applied. After overnight incubation they were imaged by fluorescence confocal microscopy using a Olympus FluoView 1000 BX2 Upright Confocal microscope. Co-localization experiments were performed by incubating cells with either FITC labeled UCHT-1 or DHFR²antiCD3+bis-MTX oligo FITC with Alexa Fluor 594 labeled transferrin (Invitrogen) for 30 minutes at 37° C. before washing and continuing slide preparation as above.

Flow Cytometry:

$1 \times 10^6$ HPB-MLT cells were treated with FITC or BODIPY labeled constructs (1/0.5/0.1 µM) at 4° C. for 1 hr in PBS buffer (containing 0.05% BSA and 0.1% sodium azide). Cells were pelleted (400×g, 10 min), washed twice, and finally resuspended in the supplemented PBS and their fluorescence was analyzed with a FACSCalibur flow cytometer (BD Biosciences). For the competition experiment, $1 \times 10^6$ HPB-MLT cells were incubated with 40 nM UCHT-1 on ice for 10 mins before addition of all the three DHFR²anti-CD3 constructs (0.1 µM). After 1 hr incubation cells were washed, resuspended and analyzed by flow cytometry. For cell specific experiments, $1 \times 10^6$ Raji cells were incubated with the constructs.

Scheme 1.S5: Flow Cytometry Competition Experiment

Competitive binding experiment where unlabelled antiCD3 mAb (UCHT-1) was used to prevent binding of fluorescently labeled construct (DHFR²antiCD3+bis-MTX oligo FITC). In the absence of UCHT-1 an increase in fluorescence is observed. Preincubation with UCHT-1 results in reduced fluorescence, similar to that of the unstained cells.

Scheme 1.S6: Concentration Dependence on Observed Fluorescence

Incubation of increasing concentrations of DHFR²antiCD3+bis-MTX oligo FITC results in increased mean fluorescence of HPB-MLT cells as analyzed by flow cytometry.

Scheme 1.S7: Cell Specificity Experiment 1 uM of fluorescently labeled construct (DHFR²antiCD3+bis-MTX oligo FITC; DHFR²antiCD3+complement FITC; DHFR²antiCD3+complement-DHFR²-BODIPY) or 20 nM FITC labeled UCHT-1 was incubated with Raji cells (B cells lacking CD3). None of the cells showed appreciable increase in fluorescence beyond that of the unstained cells.

Scheme 1.S8: Co-Localization Experiment with Alexa Fluor 594 Labeled Transferrin HPB-MLT cells were incubated with Alexa Fluor 594 labeled transferrin and either FITC labeled UCHT-1 or DHFR²antiCD3+bis-MTX oligo FITC for 30 minutes at 37° C. before being fixed and visualized by confocal microscopy. The co-localization suggests UCHT-1 and scFv-oligo construct are both localized in endosomes and are internalized by a mechanism similar to that of transferrin, which follows a clathrin dependent endocytosis mechanism.

Scheme 1.S9: Flow Cytometry Competition Experiment

Competitive binding experiment where unlabelled antiCD3 mAb (UCHT-1) was used to prevent binding of fluorescently labeled construct (DHFR²antiCD3+complement FITC). In the absence of UCHT-1 an increase in fluorescence is observed. Preincubation with UCHT-1 results in reduced fluorescence, similar to that of the unstained cells.

Scheme 1.S10: Flow Cytometry Competition Experiment

Competitive binding experiment where unlabelled antiCD3 mAb (UCHT-1) was used to prevent binding of fluorescently labeled construct (DHFR²antiCD3+complement-DHFR²-BODIPY). In the absence of UCHT-1 an increase in fluorescence is observed. Preincubation with UCHT-1 results in reduced fluorescence, similar to that of the unstained cells.

Scheme 1.S11: Concentration Dependence on Observed Fluorescence

Incubation of increasing concentrations of DHFR²antiCD3+complement FITC results in increased mean fluorescence of HPB-MLT cells as analyzed by flow cytometry.

Scheme 1.S12: Concentration Dependence on Observed Fluorescence

Incubation of increasing concentrations of DHFR²antiCD3+complement-DHFR²-BODIPY results in increased mean fluorescence of HPB-MLT cells as analyzed by flow cytometry.

Scheme 1.S13: Confocal Microscopy

Fluorescence confocal microscopy images of HPB-MLT cells treated with DHFR²antiCD3-oligo+complement-FITC and DHFR²antiCD3-oligo+complement DHFR²-BODIPY at 4° C. were also obtained.

EXAMPLE 4 DHFR-Fusion Proteins for the Cellular Delivery of Oligonucleotides and Proteins Dihydrofolate reductase (DHFR) is an enzyme that catalyzes the reduction of dihydro folic acid to tetrahydro folic acid with the help of NADPH. *E. coli* DHFR mixed with a bis-MTX ligand, which contains 2 methotrexate molecules linked by a 9-carbon linker, can lead to efficient dimerization. (Carlson, J. C. JACS (2006), 128 (23), 7630-7638) Further, bis-MTX can be linked to oligonucleotides, e.g., via a thiol-maleimide linkage to give bis-MTX-Oligo (Scheme 4.1). Furthermore, when two DHFR molecules are linked by a 13 amino acid linker, the resulting fusion protein, when incubated with a bis-MTX ligand, provides a dimeric DHFR-DHFR nanoring, whereas, if the linker is 1 amino acid long, a DHFR-DHFR octameric species is provided (Scheme 4.2). Also when a DHFR-DHFR-anti-CD3 scFv (single chain variable fragment)/cRGD is mixed with bis-MTX-Oligo, anti-CD3/cRGD nanorings decorated with oligonucleotides are obtained. When DHFR-13 a.a.-DHFR is pre-incubated with NADPH and treated with bis-MTX-oligo, it forms predominantly internal monomeric species (Scheme 4.2).

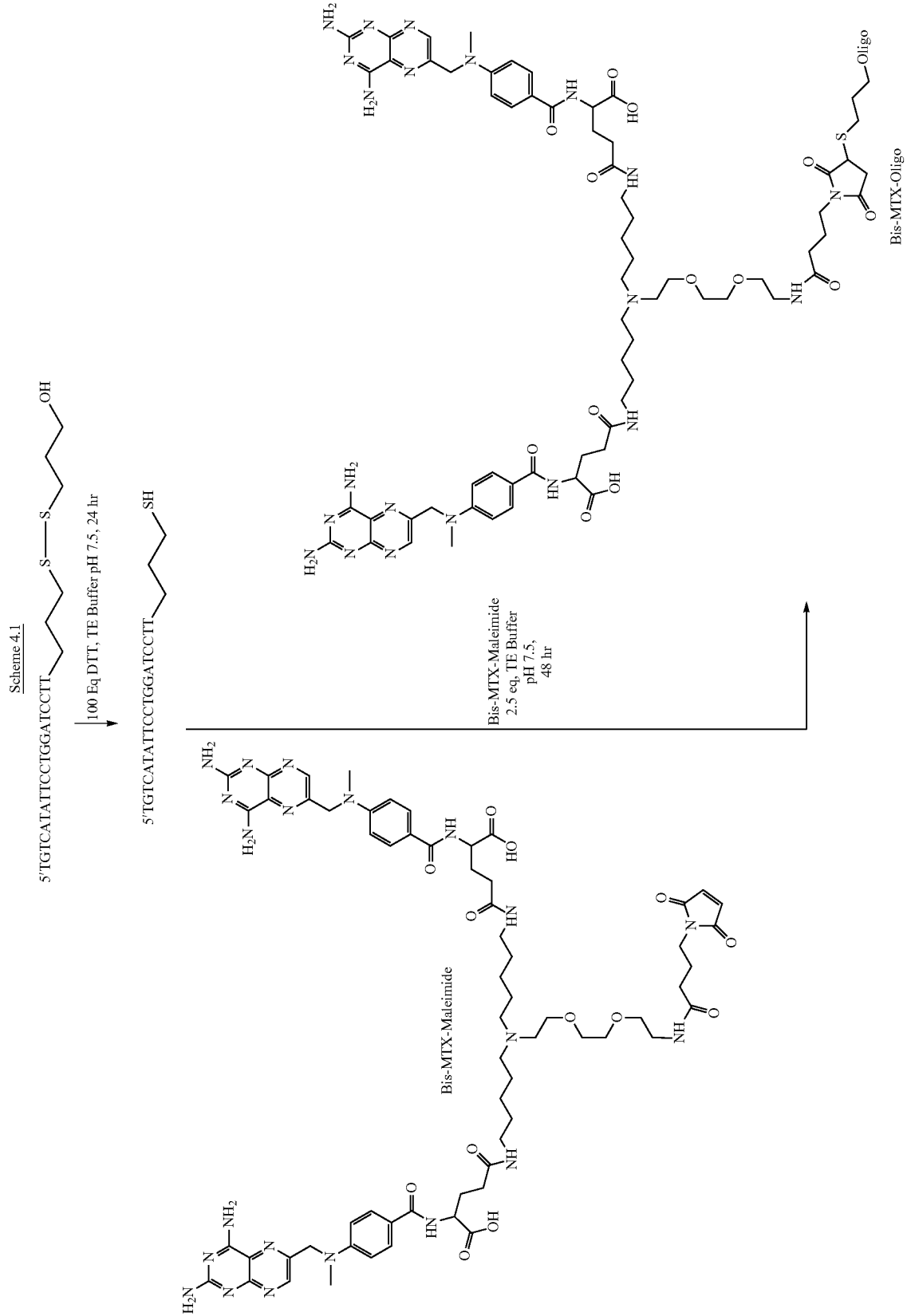

Scheme 4.2

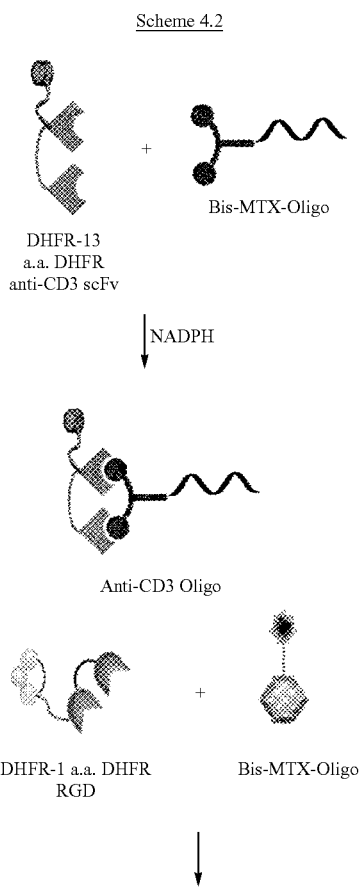

Semisynthetic oligonucleotide-protein conjugates have various applications in terms of targeted cellular delivery and nanostructures assembly. (Kang, H. Nucleic Acids Research (2008), 36 (12), 4158-4171; Duckworth, B. P. Angew. Chem. Int. Ed. (2007), 46, 8819-8822) Delivering anti-sense oligonucleotides and siRNA's into the cell is a key obstacle in this therapeutic area. Selective targeting to cancerous cells may be achieved by conjugating oligonucleotides with targeting proteins or peptides. (Song, E. Nature Biotechnology (2005), 23 (6), 709-717) As described herein, DHFR-DHFR can be fused with different targeting proteins, such as anti-CD 19, anti-CD22, EpCAM, cyclic RGD etc., thus selectively delivering oligonucleotides to different cell types. Further, by complimentary Watson-Crick base pairing of oligonucleotides, DHFR-DHFR fusion proteins can be assembled into various two and three-dimensional nanostructures, thus achieving multivalency and bispecific targeting ability.

Scheme 2.3

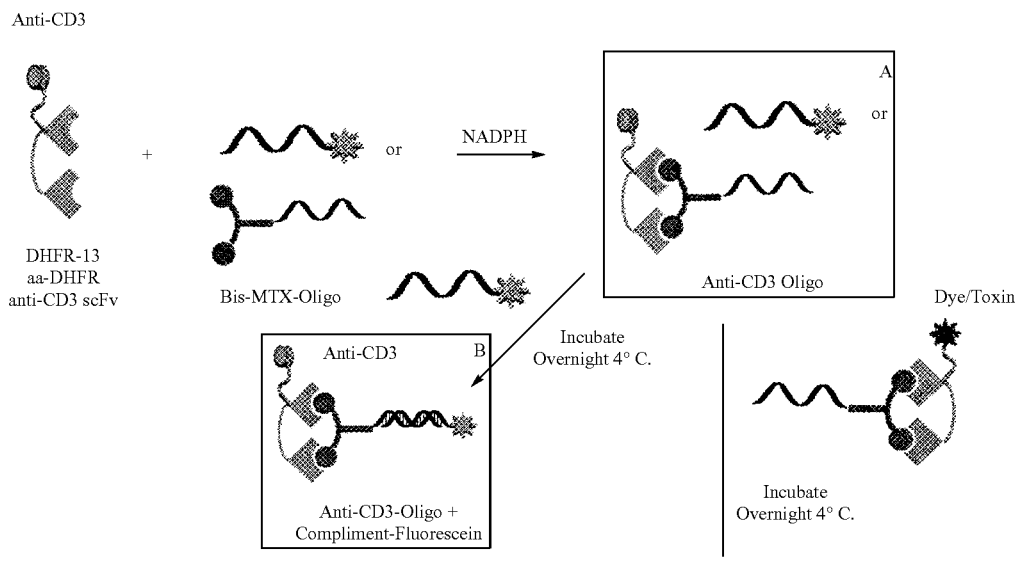

-continued

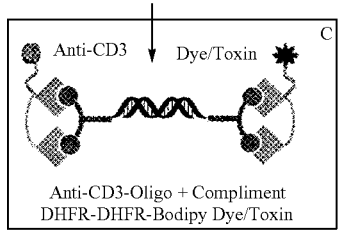

Anti-CD3-Oligo + Compliment
DHFR-DHFR-Bodipy Dye/Toxin

Currently several synthetic strategies for linking proteins to oligonucleotides have been reported. (Lu, Kui. Bioconjugate Chem. (2010), 21 (2), 187-202) Other strategies include non-covalent oligonucleotide-biotin and streptavidine conjugates, antibody hapten conjugates and aptamer. (Neimeyer, C. M. Angew. Chem. Int. Ed. (2010), 49, 1200-1216) Major problems with these approaches are site-specific conjugation, purification of the conjugates and stability of peptide/protein. Also, streptavidine fusion proteins already have biotin bound when expressed due to endogenously produced biotin by the bacterial cell. As described herein, a new method for linking oligonucleotides and proteins non-covalently via DHFR (dihydrofolate reductase) fusion proteins has been developed. One of the key advantages of this approach is that it is now possible to vary the targeting element (e.g., a protein/peptide) co-expressed with DHFR and oligonucleotide linked to bis-MTX by simply mixing the two together to provide a series of self-assembled oligonucleotides linked proteins. Various proteins have been expressed with DHFR ranging from small peptides such as cRGD to 25 kDa single chain antibodies (anti-CD3, anti-CD 19, anti-CD22), all of which can be used to target various cancerous cells.

With the help of confocal microscopy and flow cytometry, it has been demonstrated that oligonucleotide, oligo-duplex, and two different proteins linked by DNA duplex can be delivered to HPB-MLT cells (T-cells) via CD3 antigen. Further, the DHFR-RGD-eIF4E antisense Oligo octamer construct was evaluated for antisense effect in MDA-MB 231 breast cancer cell lines that over-express $\alpha_v\beta_3$ integrins. MDA-MB 231 cells has plasmid for eIF4E (eukaryotic initiation factor 4E) linked to luciferase reporter whose expression is suppressed if anti-sense oligonucleotide for eIF4E knocks down the gene. More than 70% knock down has been demonstrated when the cells were treated with 0.5 and 1 µM phosphorothiaoted anti-sense oligo as compared to untreated cells, thereby demonstrating delivery. These results are the same as non-targeted lipofectamine delivery. Further, western blot on MDA-MB 231 cells showed more than 90% knock down of eIF4E expression with 2 µM anti-sense oligo delivered in the form of DHFR-RGD-eIF4E Oligo octamer. This was comparable with the knock down obtained when 2 µM Bis-MTX-Oligo treated with lipofectamine.

With the encouraging results from above experiments, this idea will be further demonstrated by designing more 3-dimensional DNA nanostructures decorated with peptides/scFvs, and their delivery into the cells will be verified. Further, anti-CD3 and anti-EpCAM scFv's linked by DNA duplex will be evaluated for their bispecific ability towards linking cytotoxic T-cells and cancerous B-cells. Anti-CD3 and Diptheria Toxin (DT) will be linked by DNA duplex to deliver toxin to HPB-MLT cells (lymphoma T-cells). The anti-sense effect of DHFR-RGD-Oligo will be further evaluated by in-vivo tumor efficacy studies in mice tumor models.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A compound of formula I:

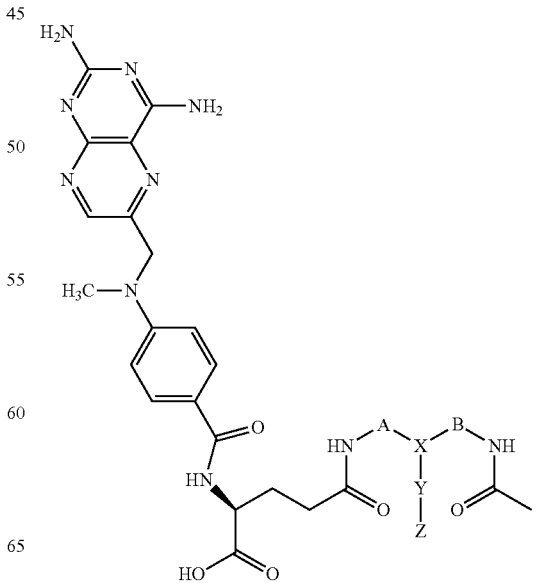

-continued

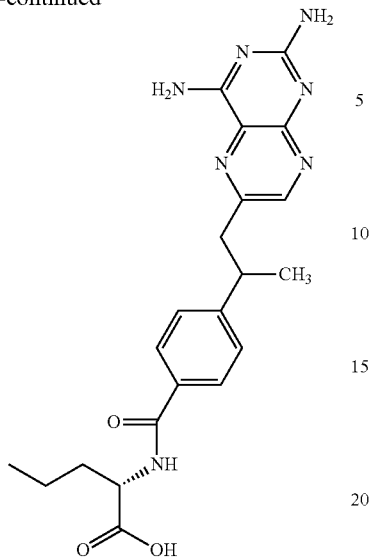

wherein:
- A is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from $(C_1\text{-}C_6)$ alkoxy, $(C_3\text{-}C_6)$cycloalkyl, $(C_1\text{-}C_6)$alkanoyl, $(C_1\text{-}C_6)$ alkanoyloxy, $(C_1\text{-}C_6)$alkoxycarbonyl, $(C_1\text{-}C_6)$alkylthio, azido, cyano, nitro, halo, hydroxy, oxo (=O), carboxy, aryl, aryloxy, heteroaryl, and heteroaryloxy;
- B is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from $(C_1\text{-}C_6)$ alkoxy, $(C_3\text{-}C_6)$cycloalkyl, $(C_1\text{-}C_6)$alkanoyl, $(C_1\text{-}C_6)$ alkanoyloxy, $(C_1\text{-}C_6)$alkoxycarbonyl, $(C_1\text{-}C_6)$alkylthio, azido, cyano, nitro, halo, hydroxy, oxo (=O), carboxy, aryl, aryloxy, heteroaryl, and heteroaryloxy;
- X is N
- Y is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from $(C_1\text{-}C_6)$ alkoxy, $(C_3\text{-}C_6)$cycloalkyl, $(C_1\text{-}C_6)$alkanoyl, $(C_1\text{-}C_6)$ alkanoyloxy, $(C_1\text{-}C_6)$alkoxycarbonyl, $(C_1\text{-}C_6)$alkylthio, azido, cyano, nitro, halo, hydroxy, oxo (=O), carboxy, aryl, aryloxy, heteroaryl, and heteroaryloxy; and
- Z is a functional group that can be used to covalently link the remainder of the compound of formula I to a therapeutic agent or an imaging agent.

2. The compound of claim 1 wherein A is a branched or unbranched $(C_2\text{-}C_{10})$alkylene chain wherein one or more carbon atoms is optionally replaced with an oxygen (—O—) atom in the chain.

3. The compound of claim 1 wherein B is a branched or unbranched $(C_2\text{-}C_{10})$alkylene chain wherein one or more carbon atoms is optionally replaced with an oxygen (—O—) atom in the chain.

4. The compound of claim 1 wherein Y is a polyethyleneoxy chain comprising 2, 3, 4, 5, 6, 7, 8, 9, or 10 repeating ethyleneoxy units.

5. The compound of claim 1, which is a compound of the following formula:

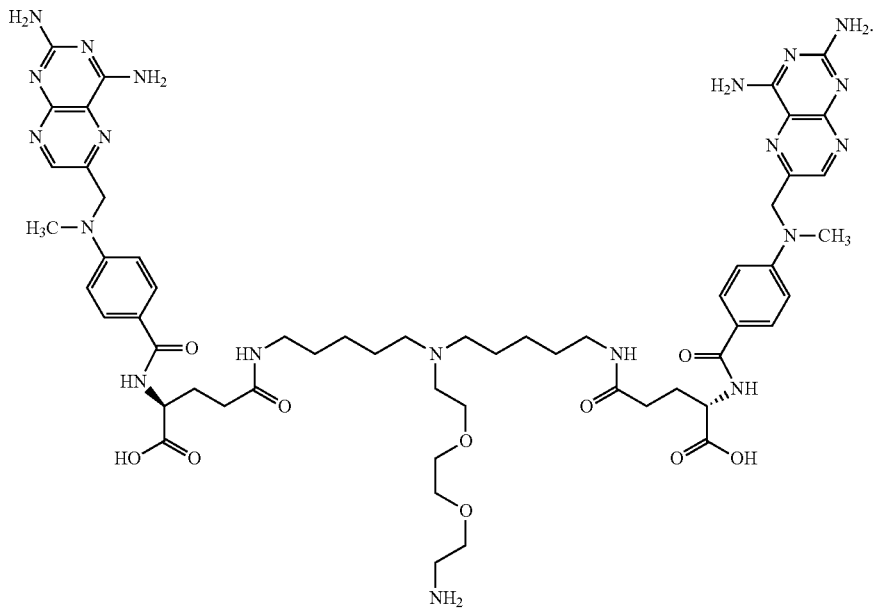

9, BisMTX-NH$_2$

6. The compound of claim 1 wherein Z is —OH, —SH, —NH$_2$, or —COOH.

7. A conjugate comprising a compound as described in claim 1 that is linked via Y to an agent, wherein the conjugate further comprises a first dihydrofolate reductase (DHFR) molecule linked to second DHFR molecule via a linker.

8. The conjugate of claim 7, wherein the conjugate further comprises a targeting molecule.

9. The conjugate of claim 8, wherein the targeting molecule selectively recognizes an antigen on a cancer cell.

10. The conjugate of claim 8, wherein the targeting molecule is a single-chain variable fragment (scFv).

11. The conjugate of any one of claim 7, wherein the agent is a first oligonucleotide.

12. The conjugate of claim 11, wherein the oligonucleotide is an antisense RNA molecule.

13. The conjugate of claim 11, wherein the conjugate further comprises a second oligonucleotide that is complementary to the first oligonucleotide, wherein the first and second oligonucleotide associate to form a duplex.

14. A composition comprising a compound as described in claim 1 and a pharmaceutically acceptable carrier.

* * * * *

UNITED STATES PATENT AND TRADEMARK OFFICE
CERTIFICATE OF CORRECTION

PATENT NO. : 9,486,535 B2  Page 1 of 1
APPLICATION NO. : 14/373209
DATED : November 8, 2016
INVENTOR(S) : Carston R. Wagner, Jae Chul Lee and Sidath C. Kumarapperuma It is certified that error appears in the above-identified patent and that said Letters Patent is hereby corrected as shown below:

In the Claims

Columns 76-77, Lines 44-67 and Lines 1-23, Claim 1, please delete the following structure:

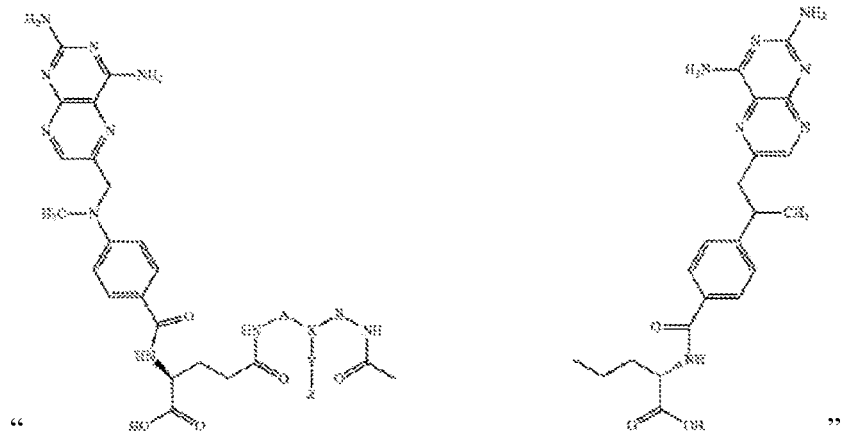

And insert:

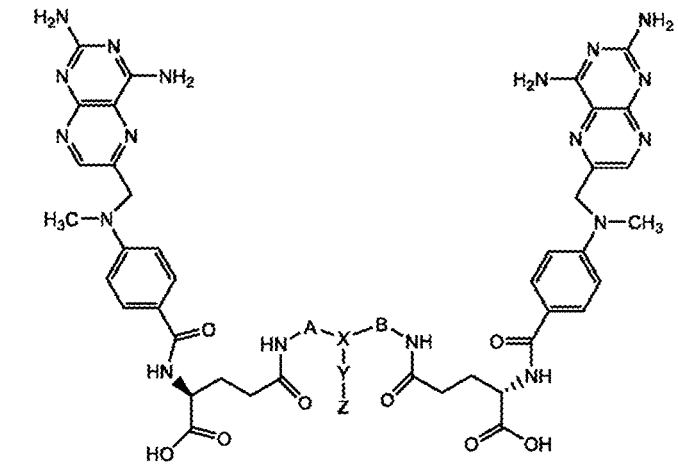

-- therefor.

Signed and Sealed this
Twenty-second Day of May, 2018

Andrei Iancu
*Director of the United States Patent and Trademark Office*